United States Patent
Lobo et al.

(10) Patent No.: US 10,384,989 B2
(45) Date of Patent: *Aug. 20, 2019

(54) COMPOSITION OF MATTER AND STRUCTURE OF ZEOLITE UZM-55 AND USE IN ISOMERIZATION OF AROMATIC MOLECULES

(71) Applicant: UOP LLC, Des Plaines, IL (US)

(72) Inventors: Rodrigo J. Lobo, Des Plaines, IL (US); Christopher P. Nicholas, Evanston, IL (US); Mark A. Miller, Niles, IL (US); Melissa M. Galey, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/814,257

(22) Filed: Nov. 15, 2017

(65) Prior Publication Data

US 2018/0170835 A1 Jun. 21, 2018

Related U.S. Application Data

(60) Provisional application No. 62/437,476, filed on Dec. 21, 2016.

(51) Int. Cl.
*C07C 5/13* (2006.01)
*C07C 5/27* (2006.01)
(Continued)

(52) U.S. Cl.
CPC ........... *C07C 5/2708* (2013.01); *B01J 29/064* (2013.01); *B01J 29/7049* (2013.01);
(Continued)

(58) Field of Classification Search
None
See application file for complete search history.

(56) References Cited

U.S. PATENT DOCUMENTS 3,201,491 A 8/1965 Stine et al.
3,626,020 A 12/1971 Neuzil
(Continued)

OTHER PUBLICATIONS

PCT Search Report dated Feb. 14, 2018 for corresponding PCT Application No. PCT/US2017/058264.

*Primary Examiner* — In Suk C Bullock
*Assistant Examiner* — Ali Z Fadhel

(57) ABSTRACT

Isomerization processes such as the isomerization of ethylbenzene and xylenes, are catalyzed by the new crystalline aluminosilicate zeolite comprising a novel framework type that has been designated UZM-55. This zeolite is represented by the empirical formula:

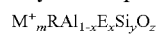

$M^+{}_m R Al_{1-x} E_x Si_y O_z$ where M represents a metal or metals selected from zinc or Group 1 (IUPAC 1), Group 2 (IUPAC 2), Group 3 (IUPAC 3) or the lanthanide series of the periodic table including sodium, potassium or a combination of sodium and potassium cations, R is an organic structure directing agent or agents derived from reactants R1 and R2 such as where R1 is diisopropanolamine and R2 is a chelating diamine, and E is an element selected from the group consisting of gallium, iron, boron and mixtures thereof. Catalysts made from UZM-55 have utility in various hydrocarbon conversion reactions.

16 Claims, 10 Drawing Sheets

(51) Int. Cl.
  *B01J 29/70* (2006.01)
  *B01J 35/00* (2006.01)
  *C07C 15/08* (2006.01)
  *G01N 23/20* (2018.01)
  *B01J 29/064* (2006.01)
  *C07C 15/073* (2006.01)

(52) U.S. Cl.
  CPC ............... *B01J 35/002* (2013.01); *C07C 5/13* (2013.01); *C07C 15/073* (2013.01); *C07C 15/08* (2013.01); *G01N 23/20075* (2013.01); *G01N 2223/418* (2013.01); *Y02P 20/52* (2015.11)

(56) References Cited

U.S. PATENT DOCUMENTS

| | | |
|---|---|---|
| 3,696,107 A | 10/1972 | Neuzil |
| 3,856,871 A | 12/1974 | Haag et al. |
| 3,856,872 A | 12/1974 | Morrison |
| 4,039,599 A | 8/1977 | Gewartowski |
| 4,184,943 A | 1/1980 | Anderson |
| 4,268,420 A | 5/1981 | Klotz |
| 4,381,419 A | 4/1983 | Wylie |
| 4,402,832 A | 9/1983 | Gerhold |
| 4,899,011 A | 2/1990 | Chu et al. |
| 4,899,012 A | 2/1990 | Sachtler |
| 4,939,110 A | 7/1990 | Sachtler et al. |
| 4,962,258 A | 10/1990 | Amelse et al. |
| 5,744,673 A | 4/1998 | Skeels et al. |
| 5,898,090 A | 4/1999 | Hammerman et al. |
| 6,143,941 A | 11/2000 | Sharma et al. |
| 6,465,705 B1 | 10/2002 | Merlen et al. |
| 6,776,975 B2 | 8/2004 | Wilson et al. |
| 6,797,849 B2 | 9/2004 | McMinn et al. |
| 6,872,866 B1 | 3/2005 | Nemeth et al. |
| 7,199,070 B2 | 4/2007 | Iwayama et al. |
| 8,058,496 B2 | 11/2011 | Bogdan et al. |
| 8,247,630 B2 | 8/2012 | Bogdan et al. |
| 8,361,435 B2 * | 1/2013 | Fecant ..................... B01J 20/10 423/706 |
| 8,623,321 B1 | 1/2014 | Miller et al. |
| 8,992,885 B2 | 3/2015 | Nicholas et al. |
| 2010/0179360 A1 | 7/2010 | Ichioka et al. |
| 2011/0245565 A1 * | 10/2011 | Bogdan .................... B01J 29/70 585/481 |
| 2012/0022279 A1 * | 1/2012 | Cabiac ..................... B01J 29/70 554/167 |
| 2015/0158020 A1 | 6/2015 | Nicholas et al. |

* cited by examiner

COMPOSITION OF MATTER AND STRUCTURE OF ZEOLITE UZM-55 AND USE IN ISOMERIZATION OF AROMATIC MOLECULES

CROSS-REFERENCE TO RELATED APPLICATION

This application claims priority from Provisional Application No. 62/437,476 filed Dec. 21, 2016, the contents of which cited application are hereby incorporated by reference in its entirety.

FIELD OF THE INVENTION

This invention relates to a zeolite having a one-dimensional channel system, 10-member rings and 12-member rings. Zeolites with this structure include a new aluminosilicate zeolite designated UZM-55. This zeolite is represented by the empirical formula:

$$M_m^{n+}R_rAl_xE_ySiO_z$$

where M represents a metal or metals from zinc or Group 1 (IUPAC 1), Group 2 (IUPAC 2), Group 3 (IUPAC 3) or the lanthanide series of the periodic table, R is an organoammonium cation such as 1,6-bis(N-methylpiperidinium) hexane and E is an element selected from the group consisting of gallium, iron, boron and mixtures thereof. UZM-55 has utility in various hydrocarbon conversion reactions such as isomerization of aromatic molecules.

BACKGROUND OF THE INVENTION

Zeolites are crystalline aluminosilicate compositions which are microporous and which are formed from corner sharing $AlO_2$ and/or $SiO_2$ tetrahedra. Numerous zeolites, both naturally occurring and synthetically prepared, are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces as well as on internal surfaces within the pore.

As used herein, zeolites may be referred to by proper name, such as UZM-39, described in U.S. Pat. No. 8,992,885, or by structure type code, such as TUN. These three letter codes indicate atomic connectivity and hence pore size, shape and connectivity for the various known zeolites. The list of these codes may be found in the ATLAS OF ZEOLITE FRAMEWORK TYPES, which is maintained by the International Zeolite Association Structure Commission at http://www.iza-structure.org/databases/. Zeolites are distinguished from each other on the basis of their composition, crystal structure and adsorption properties. One method commonly used in the art to distinguish zeolites is x-ray diffraction. UZM-55 is a zeolite with a heretofore never before described structure.

Fecant and Bats describe in U.S. Pat. No. 8,361,435 the synthesis of a product they call IZM-2 from the crystallization of a gel comprising at least one organic species R containing two quaternary nitrogen atoms with a particular XRD pattern and having a $SiO_2/Al_2O_3$ ratio preferably in the range from 60 to 600. The present invention involves a particular XRD pattern and has a $SiO_2/Al_2O_3$ ratio of greater than 75, preferably greater than 100 and most preferably greater than 150.

The xylenes, para-xylene, meta-xylene and ortho-xylene, are important intermediates that find wide and varied application in chemical syntheses. Para-xylene upon oxidation yields terephthalic acid that is used in the manufacture of synthetic textile fibers and resins. Meta-xylene is used in the manufacture of plasticizers, azo dyes, wood preservers, etc. Ortho-xylene is feedstock for phthalic anhydride production.

Xylene isomers from catalytic reforming or other sources generally do not match demand proportions as chemical intermediates, and further comprise ethylbenzene, which is difficult to separate or to convert. Para-xylene in particular is a major chemical intermediate with rapidly growing demand, but amounts to only 20% to 25% of a typical $C_8$ aromatics stream. Adjustment of isomer ratio to demand can be effected by combining xylene-isomer recovery, such as adsorption for para-xylene recovery, with isomerization to yield an additional quantity of the desired isomer. Isomerization converts a non-equilibrium mixture of the xylene isomers that is lean in the desired xylene isomer to a mixture approaching equilibrium concentrations.

In general, these xylene isomerization processes comprise contacting the xylene isomer sought to be isomerized with an isomerization catalyst under isomerization conditions. Various catalysts have been proposed for xylene isomerization. These catalysts include molecular sieves, especially molecular sieves contained in a refractory, inorganic oxide matrix. U.S. Pat. No. 4,899,012 discloses an alkylaromatic isomerization process based on a bimetallic pentasil-type zeolitic catalyst system that also produces benzene. U.S. Pat. No. 4,962,258 discloses a process for liquid phase xylene isomerization over gallium-containing, crystalline silicate molecular sieves as an improvement over aluminosilicate zeolites ZSM-5, ZSM-12 (MTW-type), and ZSM-21 as shown in U.S. Pat. No. 3,856,871. The '258 patent refers to borosilicate work, as exemplified in U.S. Pat. No. 4,268,420, and to zeolites of the large pore type such as faujasite or mordenite. U.S. Pat. No. 5,744,673 discloses an isomerization process using beta zeolite and exemplifies the use of gas-phase conditions with hydrogen. U.S. Pat. No. 5,898,090 discloses an isomerization process using crystalline silicoaluminophosphate molecular sieves. U.S. Pat. No. 6,465,705 discloses a mordenite catalyst for isomerization of aromatics that is modified by an IUPAC Group III element. U.S. Pat. No. 6,143,941, for instance, discloses oil dropped catalyst structures for xylene isomerization in which various molecular sieve structures are suggested including the MFI, MEL, EUO, FER, MFS, MTT, MTW, TON, MOR and FAU types of zeolites. The catalysts also contain a platinum group metal which may exist in the catalyst as the metal or as a compound such as an oxide, sulfide, halide or oxysulfide. U.S. Pat. Nos. 3,856,872; 4,899,011; 4,939,110 and 6,797,849 disclose, inter alia, MTW-type zeolites for xylene isomerization wherein the catalysts can contain at least one hydrogenation catalyst component.

Desirably the isomerization process performs as close to equilibrium as practical in order to maximize the para-xylene yield; however, associated with this is a greater cyclic $C_8$ loss due to side reactions. The approach to equilibrium that is used is an optimized compromise between high $C_8$ cyclic loss at high conversion (i.e., very close approach to equilibrium) and high utility costs due to the large recycle rate of unconverted $C_8$ aromatics. Catalysts thus are evaluated on the basis of a favorable balance of activity, selectivity and stability.

Due to the large scale of commercial facilities to produce para-xylene on an economically competitive basis, not only must a xylene isomerization process be active and stable, but it also must not unduly crack the aromatic feed so as to result in ring loss. Moreover, the isomerization processes produce by-products such as benzene, toluene, and aromatics having 9 or more carbon atoms. For instance, U.S. Pat. No. 6,872,866 discloses a liquid phase process using two catalysts for the isomerization of xylenes and ethylbenzene. The catalysts comprise beta zeolite and low $Si/Al_2$ MTW.

Often the xylene-containing feed to be isomerized also contains ethylbenzene. Ethylbenzene may be dealkylated such as would occur in the processes of U.S. Pat. No. 6,872,866, or the ethylbenzene can be converted. Advantageously, isomerization processes would convert ethylbenzene to xylenes. Whether the isomerization process will dealkylate or will convert ethylbenzene depends upon the isomerization process conditions including catalyst.

Catalysts for isomerization of $C_8$ aromatics ordinarily are classified by the manner of processing ethylbenzene associated with the xylene isomers. Ethylbenzene is not easily isomerized to xylenes, but is normally converted in the isomerization unit because separation from the xylenes by superfractionation or adsorption is very expensive. A widely used approach is to dealkylate ethylbenzene to form principally benzene while isomerizing xylenes to a near-equilibrium mixture. An alternative approach is to react the ethylbenzene to form a xylene mixture via conversion to and reconversion from naphthenes in the presence of a solid acid catalyst with a hydrogenation-dehydrogenation function. The former approach commonly results in higher ethylbenzene conversion, thus lowering the quantity of recycle to the para-xylene recovery unit and concomitant processing costs, but the latter approach enhances xylene yield by forming xylenes from ethylbenzene. A catalyst composite and process which enhance conversion according to the latter approach, i.e., achieve ethylbenzene isomerization to xylenes with high conversion, would effect significant improvements in xylene-production economics.

SUMMARY OF THE INVENTION

A new zeolitic material, UZM-55, has been made with a novel framework structure and which has utility in hydrocarbon processes. The present invention relates to zeolite UZM-55, the process of making it and its use as a catalyst in hydrocarbon conversion processes. Accordingly, one embodiment of the invention is a microporous crystalline zeolite having a three-dimensional framework of at least $SiO_2$ tetrahedral units and an empirical composition in the as synthesized and anhydrous basis expressed by an empirical formula of:

$$M_m^{n+}R_rAl_xE_ySiO_z$$

where M represents hydrogen or a metal or metals from zinc or Group 1 (IUPAC 1), Group 2 (IUPAC 2), Group 3 (IUPAC 3) or the lanthanide series of the periodic table, "m" is the mole ratio of M to Si and varies from 0 to about 1.0 and is usually close to zero, "n" is the weighted average valence of M and has a value of about 1 to about 3, R is a structure directing agent or agents such as 1,6-bis(N-methylpiperidinium)hexane, "r" is the mole ratio of N from the organic structure directing agent or agents to Si and has a value of about 0 to about 1.0, "x" is the mole ratio of Al to Si and has a value of from 0 to about 0.026, E is an element selected from the group consisting of gallium, iron, boron and mixtures thereof, "y" is the mole ratio of E to Si and has a value from 0 to about 0.026, and "z" is the mole ratio of O to (Al+E) and has a value determined by the equation: $z=(4+m+3\blacklozenge x+3\blacklozenge y)/2$. UZM-55 may exist as unmodified zeolite UZM-55 or as UZM-55 modified zeolite. The UZM-55 containing catalyst may take one of several forms, including for example, a spherical oil-dropped catalyst or an extruded catalyst.

An embodiment of the invention is the structure of UZM-55. The structure of UZM-55 has been solved using x-ray and electron diffraction data. The pore structure of UZM-55 is one-dimensional, where the pore contains both 10-membered and 12-membered rings. The pore is delimited by both 10-membered and 12-membered rings.

Yet another embodiment of the invention is a hydrocarbon conversion process using the zeolite of the present invention. The process comprises contacting a hydrocarbon stream with the zeolite at conversion conditions to give a converted hydrocarbon product. The hydrocarbon conversion processes include methanol to olefins, ethylene to propylene, oligomerization, isomerization of paraffins, paraffin cracking, aromatic conversions such as xylene isomerization, toluene disproportionation, ring opening and cracking to remove benzene co-boilers and alkylation of aromatics with paraffins.

DETAILED DESCRIPTION OF THE INVENTION

Figure 1:
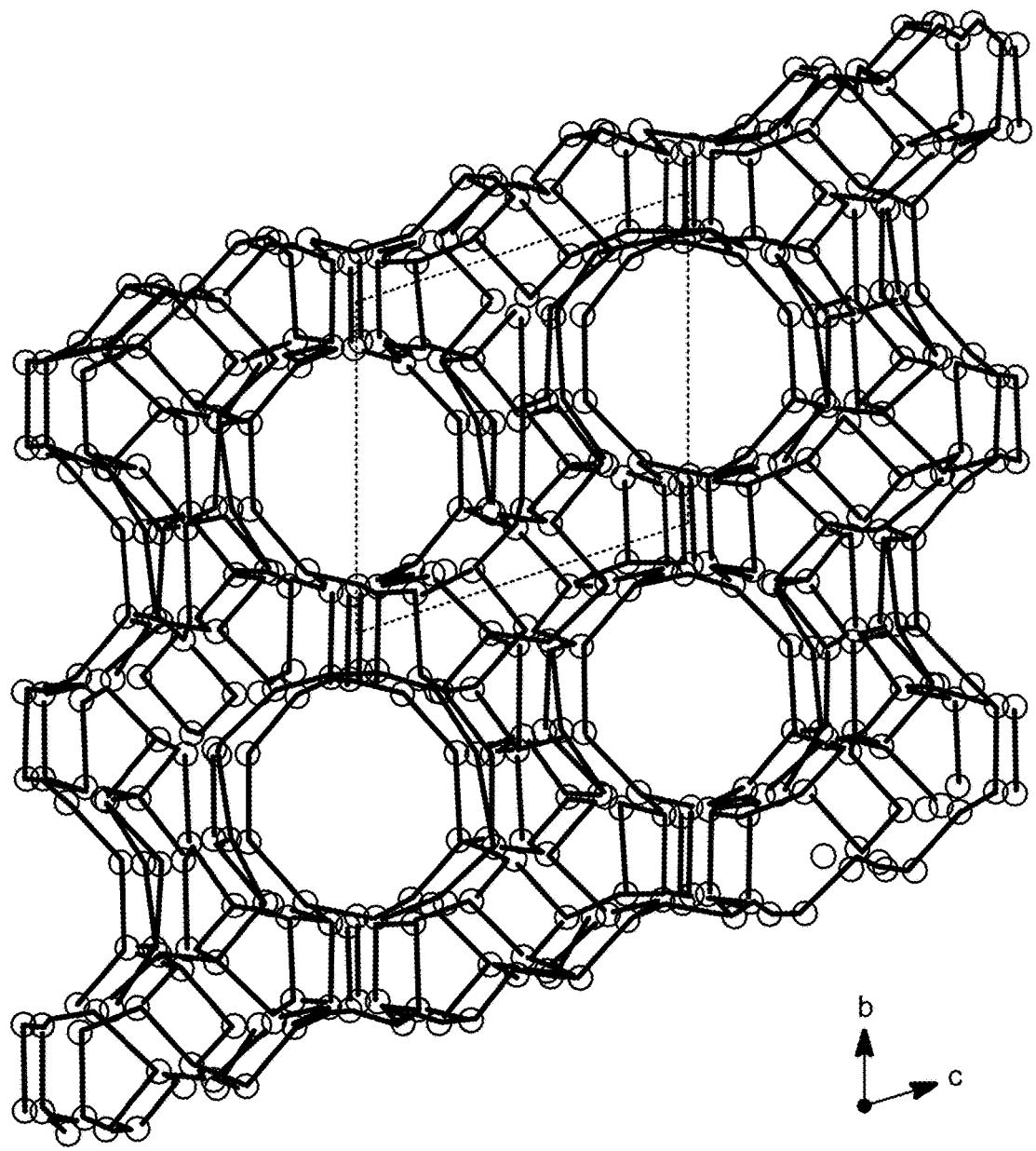
FIG. 1 shows the UZM-55 zeolite structure as a ball and stick model. Black balls are T-sites and the dashed box indicates the outline of the unit cell.

Applicants have prepared an aluminosilicate zeolite whose topological structure is novel and not described in ATLAS OF ZEOLITE FRAMEWORK TYPES, which is maintained by the International Zeolite Association Structure Commission at http://www.iza-structure.org/databases/. This new zeolite has been designated as UZM-55. As will be shown in detail, UZM-55 is different from the known zeolites in a number of its characteristics, has a novel pore topology comprising ten-membered rings and twelve-membered rings in the same pore, and finds utility as a catalyst in hydrocarbon conversion processes. A particular utility may be found in the isomerization of aromatic molecules, such as ethylbenzene, to other aromatic molecules, such as one or more xylenes selected from the group consisting of p-xylene, m-xylene, o-xylene, and combinations thereof. Zeolites may be distinguished from each other on the basis of their composition, crystal structure and adsorption properties. Channel systems for known zeolites are described in the Atlas of Zeolite Framework Types as having zero-dimensional, one-dimensional, two-dimensional or three-dimensional pore systems. A zero-dimensional pore system has no pore system running through the zeolite crystal, instead only possessing internal cages. A one-dimensional pore system contains a pore delimited by 8-membered rings or larger that run substantially down a single axis of a crystal. MTW is a known one-dimensional zeolite comprising a pore delimited by 12-membered rings running down the b axis. Two-dimensional pore (channel) containing zeolites contain intersecting pores that extend through two-dimensions of a zeolite crystal, but travel from one side of the third dimension of the zeolite crystal to the other side of the third dimension is not possible, while zeolites containing three-dimensional channel systems have a system of pores intersecting, often in a mutually orthogonal manner, such that travel from any side of a zeolite crystal to another is possible.

UZM-55 is represented in the as synthesized and anhydrous basis by the empirical formula:

$$M_m^{n+}R_rAl_xE_ySiO_z$$

where M represents hydrogen or a metal or metals from zinc or Group 1 (IUPAC 1), Group 2 (IUPAC 2), Group 3 (IUPAC 3) or the lanthanide series of the periodic table, "m" is the mole ratio of M to Si and varies from 0 to about 1.0 and is usually close to zero, "n" is the weighted average valence of M and has a value of about 1 to about 3, R is a structure directing agent or agents such as 1,6-bis(N-methylpiperidinium)hexane, "r" is the mole ratio of N from the organic structure directing agent or agents to Si and has a value of about 0 to about 1.0, "x" is the mole ratio of Al to Si and has a value of from 0 to about 0.026, E is an element selected from the group consisting of gallium, iron, boron and mixtures thereof, "y" is the mole ratio of E to Si and has a value from 0 to about 0.026, and "z" is the mole ratio of O to (Al+E) and has a value determined by the equation: $z=(4+m+3\blacklozenge x+3\blacklozenge y)/2$. Specific examples of M include but are not limited to lithium, potassium, rubidium, cesium, magnesium, calcium, strontium, barium, zinc, yttrium, lanthanum, gadolinium, and mixtures thereof. UZM-55 is characterized in that it has an x-ray diffraction pattern having at least the d-spacings and intensities set forth in Table 1.

In an embodiment, "x" may be less than 0.026 or may be less than 0.02 or may be less than 0.0133 or less than 0.003. In an embodiment, "y" may be less than 0.026 or may be less than 0.02 or may be less than 0.0133 or less than 0.003. In an embodiment, m is 0. In an embodiment, m is less than 0.05 or less than 0.1. In an embodiment, "r" has a value of from about 0.005 to about 0.08 or has a value of from about 0.01 to about 0.06.

We disclosed a process for preparing a pre-reacted aqueous solution of substituted hydrocarbons and amines incapable of undergoing pyramidal inversion, which overcomes typical difficulties to yield the structure directing agent or agents R, now published as US2015/0158020, herein incorporated by reference. Other methods of synthesizing R may be utilizable. The inventors made the surprising discovery that a substituted hydrocarbon and amine may be reacted in an aqueous solution at (or slightly above) room temperature (20° C.-80° C.) to yield an aqueous solution comprising the OSDA (organic structure directing agent). This solution may then be used without purification in the synthesis of zeolites. This procedure thereby allows the preparation of SDAs, such as unusual quaternary ammonium salts, from readily available starting reagents in a facile and practical manner.

The IUPAC definition of pyramidal inversion is given as, "a polytopal rearrangement in which the change in bond directions to a three-coordinate central atom having a pyramidal arrangement of bonds (tripodal arrangement) causes the central atom (apex of the pyramid) to appear to move to an equivalent position on the other side of the base of the pyramid. If the three ligands to the central atom are different pyramidal inversion interconverts enantiomers." The tripodal nature of many nitrogen compounds result in the ability of these compounds to undergo pyramidal inversion. Typically, the energy barrier to inversion is low for unconstrained molecules. For example, ammonia ($NH_3$) has an inversion barrier of 24.5 kJ mol$^{-1}$, with an observed inversion frequency of about $2.4*10^{10}$ s$^{-1}$, dimethylamine has an inversion barrier of 18 kJ mol$^{-1}$, triisopropylamine has an inversion barrier of 6-8 kJ mol$^{-1}$ and dimethylethylamine has an inversion barrier of 22 kJ mol$^{-1}$. However, inversion barrier energy can become very high when the nitrogen substituents are part of a small ring or other rigid molecule as in the case of 1-methylpyrrolidine. Molecules defined as essentially incapable of undergoing pyramidal inversion have an inversion barrier energy of at least about 28 kJ mol$^{-1}$ and more preferably of at least about 30 kJ mol$^{-1}$. A discussion of pyramidal inversion may be found in Rauk, A., et al., (1970), Pyramidal Inversion. ANGEW. CHEM. INT. ED. ENGL., 9: 400-414, with further discussion specifically for amines found in INORGANIC CHEMISTRY edited by Arnold F. Holleman, et al., Academic Press, 2001. Molecules may exist in many conformers or folding patterns. For example, it is well known that both chair and boat forms of cyclohexane exist and interconvert between the two different conformers. In an aspect of the invention, at least one conformer of the amine is essentially incapable of undergoing pyramidal inversion.

Organoammonium OSDAs prepared by the methods presented here are in aqueous solution and do not pose odor and flashpoint concerns. In an aspect, the invention provides a method for synthesizing an organoammonium compound. The method includes the steps of: preparing an aqueous mixture comprising water, a substituted hydrocarbon and an amine other than trimethylamine wherein the amine is a tertiary or secondary amine having 9 or less carbon atoms and being essentially incapable of undergoing pyramidal inversion, or combinations thereof; reacting the aqueous mixture; obtaining a solution comprising the organoammonium compound; and wherein the mixture and the solution are essentially free of aluminum and silicon. In one version of the method, the step of reacting the aqueous mixture occurs at a temperature from about 20° C. to about 100° C., and for a time from about 0.5 hours to about 48 hours. In another version of the method, the organoammonium product is used as a structure directing agent in the synthesis of UZM-55.

In another version of the method for synthesizing the organoammonium compound, the substituted hydrocarbon is selected from the group consisting of halogen substituted alkanes having from 2 to 8 carbon atoms, α,ω-dihalogen substituted alkanes having from 3 to 6 carbon atoms, di-halogen substituted alkanes having from 3 to 8 carbon atoms, tri-halogen substituted alkanes having from 3 to 8 carbons and combinations thereof. In another version of the method, the substituted hydrocarbon is α,ω-dihalogen substituted alkane. In another version of the method, the α,ω-dihalogen substituted alkane is selected from the group consisting of selected from the group consisting of 1,3-dichloropropane, 1,4-dichlorobutane, 1,5-dichloropentane, 1,6-dichlorohexane, 1,3-dibromopropane, 1,4-dibromobutane, 1,5-dibromopentane, 1,6-dibromohexane, 1,3-diiodopropane, 1,4-diiodobutane, 1,5-diiodopentane, 1,6-diiodohexane and combinations thereof. In another version of the method, the α,ω-dihalogen substituted alkane is selected from the group consisting of selected from the group consisting of 1,6-dichlorohexane, 1,6-dibromohexane, and 1,6-diiodohexane.

In another version of the method, the tertiary amine having 9 or fewer carbon atoms and being essentially incapable of undergoing pyramidal inversion is selected from the group consisting of 1-alkylpyrrolidines, 1-alkylpiperidines, 4-alkylmorpholines, 1-methylpiperidine, 1-ethylpyrrolidine, 1-methylpyrrolidine, and combinations thereof. The tertiary amine may be 1-methylpiperidine.

In a version of the method, the structure directing agent or agents R may have the structure of Formula 1: [bis-N,N'-diR$_1$-(piperidinium)-R$_2$]$^{2+}$2X$^-$, wherein R$_1$ is selected from H or an alkyl group having the formula C$_q$H$_{2q+1}$, where q is in the range from 1 to 4, X is halide or hydroxide, the total number of C atoms in the molecule is in the range of 11 to 24, and R$_2$ is an alkyl group having the formula C$_p$H$_{2p}$, where p is in the range from 3 to 8 and is connected to the 1 and 1' N atoms at positions s and t of the alkyl chain where s and t are independently selected from 1 to p. In an embodiment, p may be greater than 5 or equal to 5 or equal to 6. In an embodiment, q may be 1 or q may be 2. In an embodiment, X may be hydroxide. The organoammonium compound R may be 1,6-bis(N-methylpiperidinium)hexane.

The UZM-55 material is made from a reaction mixture having a composition expressed in terms of mole ratios of the oxides of:

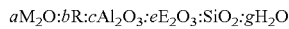

$aM_2O:bR:cAl_2O_3:eE_2O_3:SiO_2:gH_2O$ where M represents a metal or metals from hydrogen, zinc or Group 1 (IUPAC 1), Group 2 (IUPAC 2), Group 3 (IUPAC 3) or the lanthanide series of the periodic table, "a" has a value from 0 to about 0.5, R is an organic structure directing agent or agents, "b" has a value from about 0 to about 0.3, "c" has a value of from 0.0 to about 0.015, E is an element selected from the group consisting of gallium, iron, boron and mixtures thereof, "e" has a value from 0.0 to about 0.015, and "g" has a value from about 20 to about 40. The process may further comprise adding UZM-55 seeds to the reaction mixture. Sources of M include but are not limited to sodium hydroxide, potassium hydroxide, sodium aluminate, potassium aluminate, sodium silicate, and potassium silicate. In an embodiment, "a" may be less than 0.3 or less than 0.1. In an embodiment, "b" may be less than 0.25 or less than 0.2 or less than 0.15 or may be greater than 0.05 or greater than 0.1. The source of E is selected from the group consisting of alkali borates, boric acid, precipitated gallium oxyhydroxide, gallium sulfate, ferric sulfate, ferric chloride and mixtures thereof. The sources of aluminum include but are not limited to aluminum alkoxides, precipitated aluminas, aluminum metal, aluminum hydroxide, sodium aluminate, potassium aluminate, aluminum salts and alumina sols. Specific examples of aluminum alkoxides include, but are not limited to aluminum sec-butoxide and aluminum ortho isopropoxide. In an embodiment, "c" may be less than 0.01 or less than 0.008 or less than 0.005 or less than 0.0017. Sources of silica include but are not limited to tetraethylorthosilicate, colloidal silica, fumed silica, precipitated silica and alkali silicates. In an embodiment, "g" may be greater than 25 or greater than 27 or may be less than 35 or less than 30.

The reaction mixture is reacted at a temperature of about 150° to about 185° C. for a time of about 1 day to about 3 weeks in a stirred, sealed reaction vessel under autogenous pressure. After crystallization is complete, the solid product is isolated from the heterogeneous mixture by means such as filtration or centrifugation, and may be washed with deionized water and dried in air at ambient temperature at about 100° C. The reaction mixture may be reacted at a temperature of about 160° to about 175° C. for a time of about 1 day to about 3 weeks. In an embodiment, the reaction mixture is reacted at a temperature of about 160° to about 175° C. for a time of about 1 day to about 1 week.

UZM-55, in the as-synthesized and anhydrous basis, is characterized by the x-ray diffraction pattern, having at least the d-spacings and relative intensities set forth in Table 1 below. Those peaks characteristic of UZM-55 are shown in Table 1. UZM-55 is a material of quite low symmetry, so many peaks may not be a single reflection, but may actually be a combination of reflections. Additional peaks, particularly those of very weak intensity, may also be present. All peaks of medium or higher intensity present in UZM-55 are represented in Table 1. Diffraction patterns herein were obtained using a typical laboratory powder diffractometer, utilizing the K$_\alpha$ line of copper; Cu K alpha. Typical errors in two theta are 0.02. From the position of the diffraction peaks represented by the angle 2θ, the characteristic interplanar distances $d_{hkl}$ of the sample can be calculated using the Bragg equation. The intensity is calculated on the basis of a relative intensity scale attributing a value of 100 to the line representing the strongest peak on the X-ray diffraction pattern, and then: very weak (VW) means less than 15; weak (W) indicates in the range 15 to 30; weak to medium (MW) means in the range 30 to 50; medium (M) means in the range 50 to 65; strong (S) means in the range 65 to 85; very strong (VS) means more than 85. Intensities may also be shown as inclusive ranges of the above. The X-ray diffraction patterns from which the data (d spacing and intensity) are obtained are characterized by a large number of reflections some of which are broad peaks or peaks which form shoulders on peaks of higher intensity. Some or all of the shoulders may not be resolved. This may be the case for samples of low crystallinity, of particular morphological structures or for samples with crystals which are small enough to cause significant broadening of the X-rays. This can also be the case when the equipment or operating conditions used to produce the diffraction pattern differ significantly from those used in the present case.

TABLE 1

| 2θ | d(Å) | I/I₀ % |
|---|---|---|
| 7.16 | 12.34 | VW-W |
| 7.44 | 11.87 | VW-W |
| 8.58 | 10.30 | VW |
| 21.01* | 4.225 | VS |
| 22.07 | 4.024 | VW |
| 22.75 | 3.906 | MW-M |
| 24.19 | 3.676 | VW |
| 26.41 | 3.372 | VW-W |
| 32.73 | 2.734 | VW |
| 36.37 | 2.468 | VW |
| 44.01 | 2.056 | VW |

In particular, the very strong peak at 4.22 Å is a composite peak of at least two peaks as indicated by the asterisk. In an embodiment, the peak at d=4.22 Å is the strongest peak. In an embodiment, only 1 peak of very strong intensity exists. In an embodiment, no more than 2 peaks of greater than 30 intensity exist.

As will be shown in detail in the examples, the UZM-55 material is thermally stable up to a temperature of at least 600° C. and in another embodiment, up to at least 800° C.

In an embodiment, the $SiO_2/Al_2O_3$ ratio of UZM-55 may be greater than 75 or greater than 100 or greater than 150 or greater than 600. In an aspect, UZM-55 is difficult to crystallize at low $SiO_2/Al_2O_3$ ratios. MTW and other competing phases may crystallize in lieu of UZM-55 at $SiO_2/Al_2O_3$ ratios of less than about 80.

As synthesized, the UZM-55 material will contain some exchangeable or charge balancing cations in its pores. These exchangeable cations can be exchanged for other cations, or in the case of organic SDAs, they can be removed by heating under controlled conditions. It may be possible to remove some organic SDAs from the UZM-55 zeolite directly by ion exchange. The UZM-55 zeolite may be modified in many ways to tailor it for use in a particular application. Modifications include calcination, ion-exchange, steaming, various acid extractions, ammonium hexafluorosilicate treatment, or any combination thereof, as outlined for the case of UZM-4M in U.S. Pat. No. 6,776,975 B1 which is incorporated by reference in its entirety. Conditions may be more severe than shown in U.S. Pat. No. 6,776,975. Properties that are modified include porosity, adsorption, Si/Al ratio, acidity, thermal stability, and the like.

After calcination and on an anhydrous basis, the microporous crystalline zeolite UZM-55 has a three-dimensional framework of at least $AlO_2$ and $SiO_2$ tetrahedral units and an empirical composition in the hydrogen form expressed by an empirical formula of

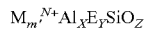

$$M_{m'}^{N+}Al_xE_YSiO_Z$$

where "m'" is the mole ratio of M to Si and varies from 0 to about 1.0 and is usually close to zero, "N" is the weighted average valence of M and has a value of about +1 to about +3, "X" is the mole ratio of Al to Si and has a value of from 0 to about 0.026, E is an element selected from the group consisting of gallium, iron, boron and mixtures thereof, "Y" is the mole ratio of E to Si and has a value from 0 to about 0.026, and "Z" is the mole ratio of O to (Al+E) and has a value determined by the equation: z=(4+m+3◆x+3◆y)/2.

In an embodiment, "X" may be less than 0.026 or may be less than 0.02 or may be less than 0.0133 or less than 0.003. In an embodiment, "Y" may be less than 0.026 or may be less than 0.02 or may be less than 0.0133 or less than 0.003. In an embodiment, m' is 0. In an embodiment, m' is less than 0.05 or less than 0.1.

In the calcined form, UZM-55 displays the XRD pattern shown in Table 2. Those peaks characteristic of UZM-55 are shown in Table 2. Additional peaks, particularly those of very weak intensity, may also be present. All peaks of medium or higher intensity present in UZM-55 are represented in Table 2.

TABLE 2

| 2θ | d(Å) | I/I₀ % |
|---|---|---|
| 7.19 | 12.28 | MW-S |
| 7.57 | 11.67 | W-M |
| 8.59 | 10.29 | W-MW |
| 14.72 | 6.013 | VW |
| 21.04* | 4.219 | VS |
| 22.15 | 4.010 | VW |
| 23.03 | 3.859 | MW-M |
| 24.34 | 3.654 | VW |
| 26.63 | 3.345 | VW-W |
| 36.47 | 2.462 | VW |
| 44.49 | 2.035 | VW |

The intensity is calculated on the basis of a relative intensity scale attributing a value of 100 to the line representing the strongest peak on the X-ray diffraction pattern, and relative intensities are described above. In particular, the very strong peak at 4.22 Å is a composite peak of at least two peaks as indicated by the asterisk.

In an embodiment, the peak at d=4.22 Å is the strongest peak. In an embodiment, only the peak at d=4.22 Å is of very strong intensity. In an embodiment, the difference in d space between the first peak of greater than very weak intensity at 12.28 Å and the very strong peak at d=4.22 Å is greater than 7.9 Å or greater than 8.02 Å or greater than 8.04 Å and may be less than 9.0 Å or less than 8.5 Å or less than 8.2 Å. In an embodiment, the absolute value of the difference in 2-theta between the first peak of greater than very weak intensity at 7.19° 2θ and the very strong peak at 21.04° 2θ is less than 13.90 or less than 13.88 and may be greater than 13.6 or greater than 13.7 or greater than 13.8. In an embodiment, the difference in d space between the first peak of greater than very weak intensity at 12.28 Å and the second peak of greater than very weak intensity at d=11.67 Å is greater than 0.50 Å or greater than 0.55 Å or greater than 0.58 Å or greater than 0.60 Å and may be less than 0.70 Å or less than 0.66 Å or less than 0.63 Å. In an embodiment, the absolute value of the difference in 2 theta between the first peak of greater than very weak intensity at 7.19° 2θ and the second peak of greater than very weak intensity at 7.57° 2θ is greater than 0.33 or greater than 0.34 Å or greater than 0.36 or greater than 0.37 and may be less than 0.50 or less than 0.45 or less than 0.40.

Also as shown in the examples, as measured by the BET technique using $N_2$ as the adsorbing gas, UZM-55 may have a micropore volume of greater than 0.08 mL/g or greater than 0.10 mL/g or greater than 0.11 mL/g and may have a micropore volume of less than 0.15 mL/g or less than 0.14 mL/g or less than 0.13 mL/g.

Figure 2:
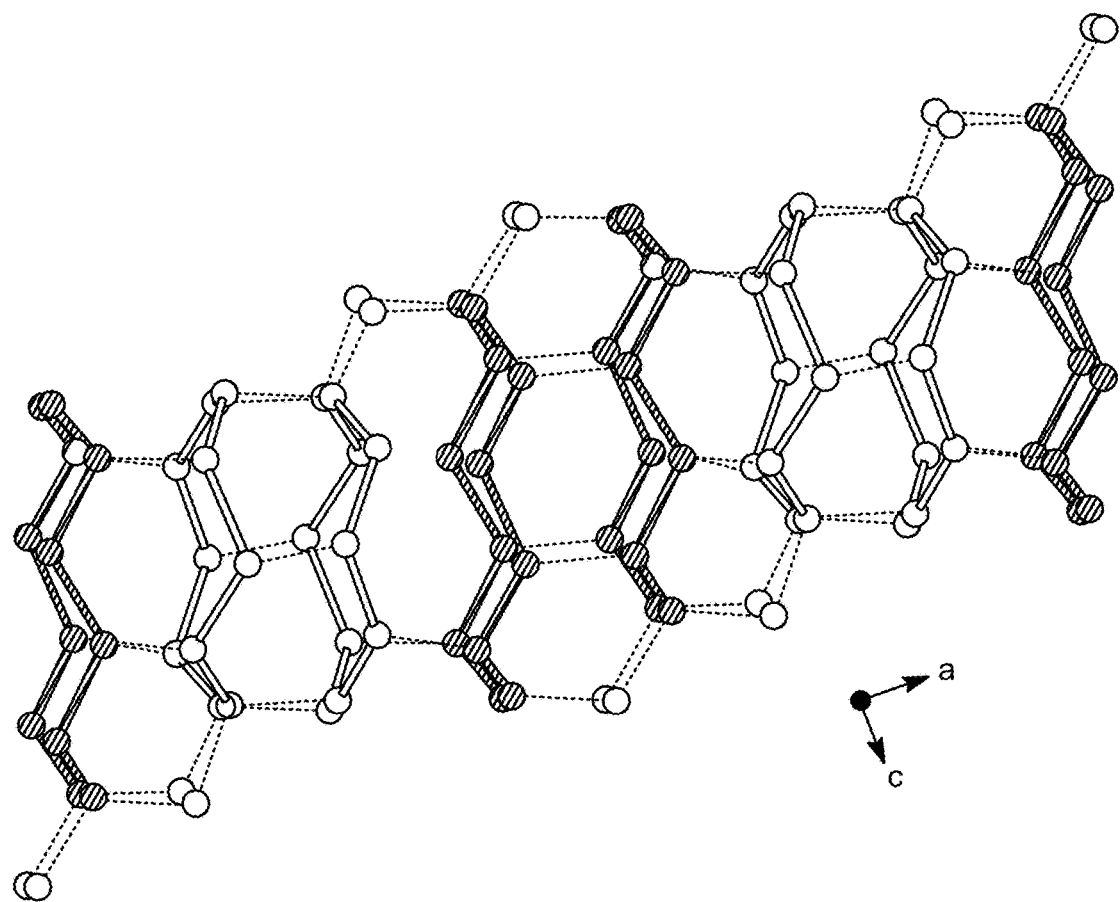
FIG. 2 shows the UZM-55 pore structure perpendicular to the pore. 12-membered rings are indicated in black, 10-membered rings in gray, T-sites not in a ring forming connections between rings in white, and connections between T-sites in dashed lines.

The structure of UZM-55 has been solved using x-ray diffraction, electron diffraction, TEM, model building and Rietveld refinement. Using these techniques, we determined that UZM-55 may possess a unit cell of a=17.80 Å, b=12.23 Å, c=12.93 Å, alpha=71.79°, beta=88.16°, gamma=90.25°. Typical error in the unit cell is ±0.75 Å or about ±0.5 Å on distances and about ±1.0° on angles. The unit cell was proposed from transmission electron diffraction experiments and confirmed by x-ray diffraction. UZM-55 was found to possess a unique triclinic unit cell and t-site connectivity not found in previously described zeolitic materials. Framework models were proposed starting from dislocated MTW frameworks and refined against the x-ray diffraction data. Model building and refinement/optimization methods were then utilized to obtain the final three-dimensionally connected model. UZM-55 is a synthetic porous crystalline material possessing a unique one-dimensional channel system which is defined by 10-membered rings of tetrahedrally coordinated atoms and 12-membered rings of tetrahedrally coordinated atoms. In an aspect, the pore structure is one-dimensional and delimited by both ten-membered rings and twelve-membered rings. FIG. 1 shows the UZM-55 zeolite structure as a ball and stick model. Black balls are T-sites and the dashed box indicates the outline of the unit cell. This view is down the a-axis, viewing through the 10- and 12-membered ring pore. FIG. 2 shows the UZM-55 pore structure perpendicular to the pore. Here, twelve-membered rings are indicated in black, ten-membered rings are indicated in gray, T-sites forming bridging connections between rings are indicated in white, and connections between T-sites are indicated in dashed lines. A ten-membered ring is followed by a ten-membered ring which is followed by a twelve-membered ring which is followed by a twelve-membered ring before the pattern repeats as one progresses down the pore. Each pair of ten-membered rings is followed by a pair of twelve-membered rings which is followed by a pair of ten-membered rings, etc. as one progresses down the one-dimensional pore. Thus, the one-dimensional pore is delimited by both ten-membered rings and twelve-membered rings.

Figure 3:
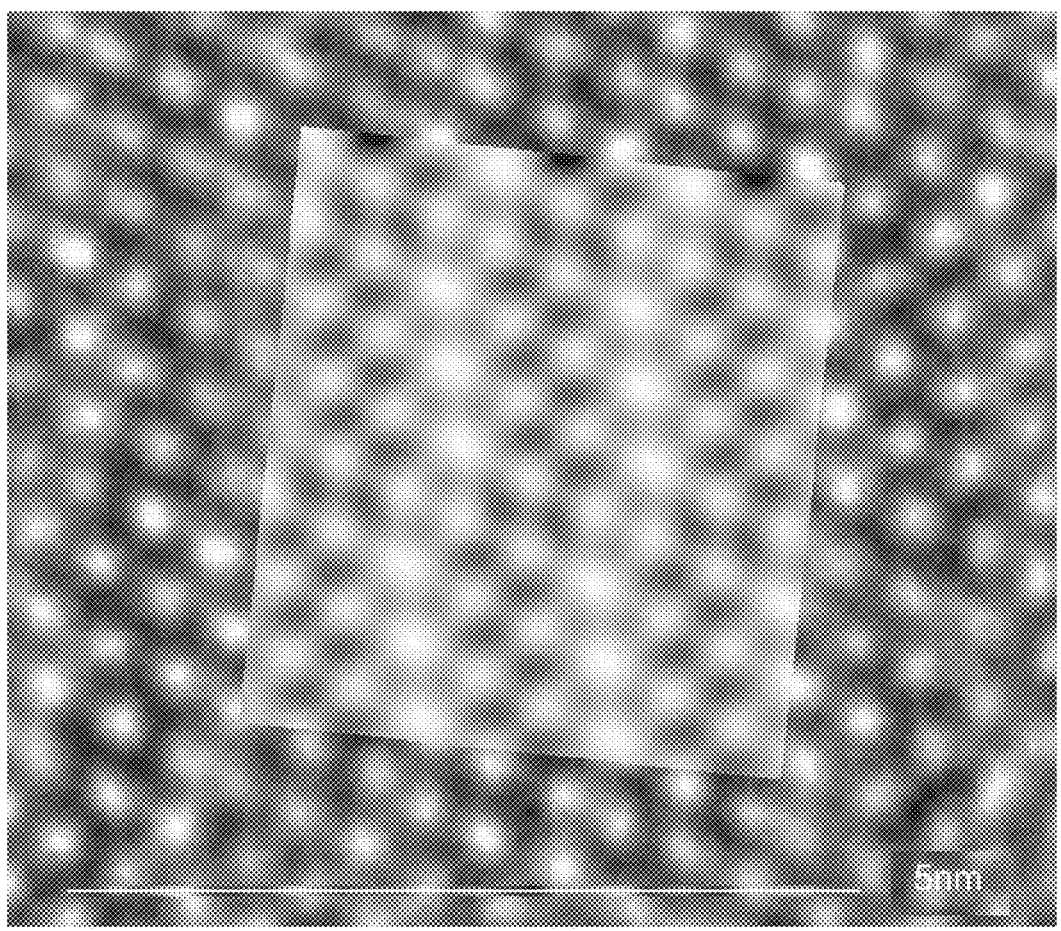
FIG. 3 shows a TEM image of UZM-55 along [0, −1, 0] showing regions of light and dark contrast along with an overlay of the expected contrast generated from the structure solution via a blurred, contrast-inverted projected potential.

FIG. 3 shows an experimental TEM image of UZM-55 along [0, −1, 0] showing regions of light and dark contrast along with an overlay of the expected contrast generated from the structure solution via a blurred, contrast-inverted projected potential. The areas of light contrast undulate through the structure and correspond to the undulation of the 1-dimensional channel running perpendicular to this view. The calculated, expected, TEM image overlaid in FIG. 3 shows the same areas of light and dark contrast as that observed in the experimental image.

The structure of UZM-55 may be defined by its unit cell, the smallest structural unit containing all the structural elements of the material. UZM-55 comprises a framework of tetrahedral atoms (T-atoms) bridged by oxygen atoms, the tetrahedral atom framework defined by the unit cell described above, or less symmetric variants thereof, with atomic coordinates as shown in Table 3 or Table 4, wherein each coordinate position may vary within ±0.75 Å. T-atoms are understood to indicate Si, Al or E atoms. Coordinates in the tables are shown as a fraction of the unit cell, hence site T1 is at a position 16.25 Å, 3.30 Å, 9.63 Å from the origin of the unit cell. Table 3 shows the T-positions of the calcined form of UZM-55 as optimized with the LAMMPS package using the Universal Force Field (UFF) applied via the Scienomics MAPS platform.

TABLE 3

| Calcined, optimized | | | |
|---|---|---|---|
| Site | X | Y | Z |
| T1 | 0.913(3) | 0.270(4) | 0.745(4) |
| T2 | 0.001(3) | 0.121(4) | 0.633(4) |
| T3 | 0.995(3) | 0.512(4) | 0.373(4) |
| T4 | 0.911(3) | 0.129(4) | 0.983(4) |
| T5 | 0.347(3) | 0.135(4) | 0.940(4) |
| T6 | 0.623(3) | 0.208(4) | 0.828(4) |

TABLE 3-continued

| Calcined, optimized | | | |
|---|---|---|---|
| Site | X | Y | Z |
| T7 | 0.432(3) | 0.507(4) | 0.581(4) |
| T8 | 0.247(3) | 0.697(4) | 0.335(4) |
| T9 | 0.275(3) | 0.466(4) | 0.500(4) |
| T10 | 0.462(3) | 0.278(4) | 0.765(4) |
| T11 | 0.185(3) | 0.223(4) | 0.870(4) |
| T12 | 0.167(3) | 0.456(4) | 0.701(4) |
| T13 | 0.164(3) | 0.094(4) | 0.694(4) |
| T14 | 0.709(3) | 0.175(4) | 0.498(4) |
| T15 | 0.550(3) | 0.239(4) | 0.417(4) |
| T16 | 0.280(3) | 0.212(4) | 0.514(4) |
| T17 | 0.434(3) | 0.141(4) | 0.606(4) |
| T18 | 0.075(3) | 0.106(4) | 0.057(4) |
| T19 | 0.089(3) | 0.103(4) | 0.296(4) |
| T20 | 0.792(3) | 0.143(4) | 0.164(4) |
| T21 | 0.523(3) | 0.103(4) | 0.262(4) |
| T22 | 0.639(3) | 0.109(4) | 0.081(4) |
| T23 | 0.253(3) | 0.070(4) | 0.364(4) |
| T24 | 0.369(3) | 0.038(4) | 0.192(4) |
| T25 | 0.012(3) | 0.742(4) | 0.610(4) |
| T26 | 0.826(3) | 0.286(4) | 0.313(4) |
| T27 | 0.086(3) | 0.729(4) | 0.254(4) |
| T28 | 0.998(3) | 0.879(4) | 0.367(4) |
| T29 | 0.004(3) | 0.487(4) | 0.626(4) |
| T30 | 0.088(3) | 0.870(4) | 0.016(4) |
| T31 | 0.653(3) | 0.864(4) | 0.059(4) |
| T32 | 0.376(3) | 0.791(4) | 0.171(4) |
| T33 | 0.567(3) | 0.492(4) | 0.418(4) |
| T34 | 0.752(3) | 0.302(4) | 0.664(4) |
| T35 | 0.724(3) | 0.534(4) | 0.499(4) |
| T36 | 0.537(3) | 0.721(4) | 0.234(4) |
| T37 | 0.814(3) | 0.776(4) | 0.129(4) |
| T38 | 0.832(3) | 0.543(4) | 0.299(4) |
| T39 | 0.835(3) | 0.905(4) | 0.305(4) |
| T40 | 0.290(3) | 0.824(4) | 0.501(4) |
| T41 | 0.449(3) | 0.760(4) | 0.582(4) |
| T42 | 0.719(3) | 0.787(4) | 0.485(4) |
| T43 | 0.565(3) | 0.858(4) | 0.393(4) |
| T44 | 0.924(3) | 0.893(4) | 0.942(4) |
| T45 | 0.910(3) | 0.896(4) | 0.704(4) |
| T46 | 0.207(3) | 0.856(4) | 0.835(4) |
| T47 | 0.476(3) | 0.896(4) | 0.737(4) |
| T48 | 0.360(3) | 0.890(4) | 0.918(4) |
| T49 | 0.746(3) | 0.929(4) | 0.635(4) |
| T50 | 0.630(3) | 0.961(4) | 0.807(4) |
| T51 | 0.987(3) | 0.257(4) | 0.389(4) |
| T52 | 0.173(3) | 0.713(4) | 0.686(4) |

Table 4 shows the T-atom positions resulting from the Rietveld refinement of the x-ray data of the calcined form of UZM-55.

TABLE 4

| Rietveld refinement results | | | |
|---|---|---|---|
| Site | X | Y | Z |
| T1 | 0.906(3) | 0.259(4) | 0.751(4) |
| T2 | 0.093(3) | 0.740(4) | 0.248(4) |
| T3 | 0.018(3) | 0.119(4) | 0.648(4) |
| T4 | 0.981(3) | 0.880(4) | 0.351(4) |
| T5 | 0.005(3) | 0.504(4) | 0.376(4) |
| T6 | 0.994(3) | 0.495(4) | 0.623(4) |
| T7 | 0.907(3) | 0.123(4) | 0.984(4) |
| T8 | 0.092(3) | 0.876(4) | 0.015(4) |
| T9 | 0.337(3) | 0.141(4) | 0.932(4) |
| T10 | 0.662(3) | 0.858(4) | 0.067(4) |
| T11 | 0.639(3) | 0.204(4) | 0.804(4) |
| T12 | 0.360(3) | 0.795(4) | 0.195(4) |
| T13 | 0.431(3) | 0.510(4) | 0.579(4) |
| T14 | 0.568(3) | 0.489(4) | 0.420(4) |
| T15 | 0.239(3) | 0.709(4) | 0.355(4) |
| T16 | 0.760(3) | 0.290(4) | 0.645(4) |
| T17 | 0.275(3) | 0.479(4) | 0.494(4) |

TABLE 4-continued

Rietveld refinement results

| Site | X | Y | Z |
|---|---|---|---|
| T18 | 0.724(3) | 0.520(4) | 0.505(4) |
| T19 | 0.464(3) | 0.267(4) | 0.741(4) |
| T20 | 0.535(3) | 0.732(4) | 0.258(4) |
| T21 | 0.199(3) | 0.233(4) | 0.855(4) |
| T22 | 0.800(3) | 0.767(4) | 0.144(4) |
| T23 | 0.166(3) | 0.467(4) | 0.691(4) |
| T24 | 0.833(3) | 0.532(4) | 0.308(4) |
| T25 | 0.179(3) | 0.096(4) | 0.694(4) |
| T26 | 0.820(3) | 0.903(4) | 0.305(4) |
| T27 | 0.725(3) | 0.149(4) | 0.485(4) |
| T28 | 0.274(3) | 0.851(4) | 0.514(4) |
| T29 | 0.565(3) | 0.218(4) | 0.417(4) |
| T30 | 0.434(3) | 0.781(4) | 0.582(4) |
| T31 | 0.273(3) | 0.204(4) | 0.506(4) |
| T32 | 0.726(3) | 0.795(4) | 0.493(4) |
| T33 | 0.433(3) | 0.136(4) | 0.586(4) |
| T34 | 0.566(3) | 0.863(4) | 0.413(4) |
| T35 | 0.068(3) | 0.138(4) | 0.010(4) |
| T36 | 0.931(3) | 0.861(4) | 0.989(4) |
| T37 | 0.074(3) | 0.093(4) | 0.277(4) |
| T38 | 0.925(3) | 0.906(4) | 0.722(4) |
| T39 | 0.801(3) | 0.139(4) | 0.175(4) |
| T40 | 0.198(3) | 0.860(4) | 0.824(4) |
| T41 | 0.537(3) | 0.098(4) | 0.235(4) |
| T42 | 0.462(3) | 0.902(4) | 0.764(4) |
| T43 | 0.653(3) | 0.113(4) | 0.068(4) |
| T44 | 0.346(3) | 0.886(4) | 0.931(4) |
| T45 | 0.241(3) | 0.072(4) | 0.356(4) |
| T46 | 0.758(3) | 0.927(4) | 0.643(4) |
| T47 | 0.370(3) | 0.057(4) | 0.182(4) |
| T48 | 0.629(3) | 0.942(4) | 0.817(4) |
| T49 | 0.002(3) | 0.761(4) | 0.593(4) |
| T50 | 0.997(3) | 0.238(4) | 0.406(4) |
| T51 | 0.833(3) | 0.267(4) | 0.318(4) |
| T52 | 0.166(3) | 0.732(4) | 0.681(4) |

Tables 3 and 4 are shown with 52 T-sites. If the structure of UZM-55 is set in the space group P1 (#1), 52 independent T-sites are present. If the space group P−1 (#2) is instead utilized, an inversion center is present and only 26 independent T-sites are present although 52 T-sites still exist in a single unit cell. In an aspect, the structure of UZM-55 may be described in either the P1 or P−1 space group.

In an aspect, UZM-55 may comprise a faulted material. The UZM-55 of the current invention may possess planar faults consistent with streaking of reflections in electron diffraction images and asymmetric broadening of XRD patterns. The faulting may be visible in TEM images of UZM-55 when viewing down the 100 axis. The faulting may be consistent with an offset of ~⅓ of the b axis. In the MTW zeolite structure, a planar fault is known with a plane across the middle of the twelve-ring pore. For the case of the structure of UZM-55, a similar fault plane exists through the middle of the pore system (the a-b-plane), however, due to the low symmetry of UZM-55, the fault in UZM-55 is more likely a translation of the "butterfly unit" in the c-direction coupled with an inversion in the b-direction. These operations allow the $5^4 6$ "butterfly unit" to invert while the t-site connectivity is preserved. In crystallographic terms this faulting operation could be considered as a c-glide perpendicular to the b-axis which would generate a monoclinic unit cell if the fault were to occur 100% of the time. Butterfly units have a 6-ring which can be viewed as the body of a butterfly and four 5-rings which serve as the wings. Zeolite structures comprising butterfly units are discussed in Guo, et. al., Z. Kristallogr. 2015, 230, 301-9. Faulting in a zeolite structure may occur randomly or in a clustered fashion. In an aspect, the faulting in the UZM-55 structure may be random.

In an aspect, faulting may occur about 20% of the time. Faulting may occur from 0% to about 100% of the time or may occur from 0% to about 50% of the time or may occur from 0% to about 30% of the time.

The crystalline UZM-55 zeolite of this invention may be used for isomerization of aromatic molecules. In an aspect, the crystalline UZM-55 zeolite may be used for converting ethylbenzene to mixtures of xylenes comprising ortho-xylene, meta-xylene and para-xylene.

Generally the feedstream may comprise $C_8$ aromatics with an ethylbenzene content of about 1 to about 60, preferably, about 1 wt-% to about 50 wt-%; an ortho-xylene content of from 0 wt-% to about 35 wt-%; a meta-xylene content of from 0 to about 95 wt % or from 20 wt-% to about 95 wt-% and a para-xylene content of from 0 to about 30 wt-% or about 25 wt % or about 20 wt % or about 15 wt %. The feedstream may also comprise other hydrocarbons which have boiling points in the range of the $C_8$ aromatic molecules. A $C_8$ aromatics feed to the present process may comprise nonaromatic hydrocarbons, i.e., naphthenes and paraffins, in an amount up to about 30 wt-%, and may contain naphthenes in an amount sufficient to enhance the ethylbenzene conversion. Naphthenes are cyclic paraffins and may include, for purposes herein, cyclic compounds having non-aromatic unsaturation in the ring structure. A convenient source of naphthenes is the isomerization process itself which produces naphthenes. Typically the naphthenes that are recycled are monocyclic compounds, especially 5 and 6 carbon atom rings, having from 5 to 9 carbon atoms. In an aspect, the naphthenes have 8 carbon atoms. The downstream unit operations will define the composition and amount of naphthenes being recycled. Generally, naphthenes may be present in the feedstream in an amount from 0 to about 40 wt % or from about 2 to about 20 wt %, or from about 4 to about 15, wt-% of the feed. Equilibria may exist under isomerization conditions between naphthenes and aromatics. Thus, at isomerization conditions that convert a greater percentage of ethylbenzene, greater concentrations of naphthenes are preferred. As the naphthenes are a by-product of the isomerization, in an aspect, the isomerization unit may be started up with the xylene and ethylbenzene feed and then the sought amount of naphthenes may be permitted to build up for steady-state operation.

In an aspect, the $C_8$ aromatics are a non-equilibrium mixture, i.e., at least one $C_8$ aromatic isomer is present in a concentration that differs substantially from the equilibrium concentration at isomerization conditions. Usually the non-equilibrium mixture is prepared by removal of para-, ortho- and/or meta-xylene from a fresh $C_8$ aromatic mixture obtained from an aromatics-production process. In an aspect, by passing the feedstream over the catalyst comprising UZM-55, the non-equilibrium $C_8$ aromatics are isomerized to a composition closer to equilibrium. In a further aspect, a feedstream high in ethylbenzene content is converted to a product stream lower in ethylbenzene content and higher in xylene content. In an aspect, a feedstream low in p-xylene content is converted to a product stream higher in p-xylene content.

The feedstream, preferably a non-equilibrium mixture of $C_8$ aromatics, is contacted with the isomerization catalyst at suitable alkylaromatic-isomerization conditions. Such conditions comprise a temperature ranging from about 0° to about 600° C. or from about 100 to about 500° C. or from about 150 to about 450° C., or from about 300 to about 500° C. The pressure generally is from about 1 to about 100 atmospheres absolute, or may be less than about 50 atmospheres, say, about 10 kPa to about 5 MPa absolute, preferably from about 100 kPa to about 3 MPa absolute. Sufficient catalyst is contained in the isomerization zone to provide a liquid hourly space velocity with respect to the hydrocarbon feed mixture of from about 0.1 to 30 hr$^{-1}$, and preferably 0.5 to 10 hr$^{-1}$. The hydrocarbon feed mixture optimally is reacted in admixture with hydrogen at a hydrogen/hydrocarbon mole ratio of about 0.5:1 to about 25:1 or more, say, between about 0.5:1 to 6:1, preferably about 1.5:1 to 5:1. One of the advantages of the processes of this invention is that relatively low partial pressures of hydrogen are still able to provide the sought selectivity and activity of the isomerization and ethylbenzene conversion. Other inert diluents such as nitrogen, argon and light hydrocarbons may be present.

The isomerization conditions may be such that the isomerization is conducted in the liquid, vapor or at least partially vaporous phase. For convenience in hydrogen distribution, the isomerization is preferably conducted in at least partially in the vapor phase. When conducted at least partially in the vaporous phase, the partial pressure of $C_8$ aromatics in the reaction zone is preferably such that at least about 50 mass-% of the $C_8$ aromatics would be expected to be in the vapor phase. Often the isomerization is conducted with essentially all the $C_8$ aromatics being in the vapor phase.

Without being bound by theory, it is thought that the reaction proceeds via the mechanism of isomerizing xylenes while reacting ethylbenzene to form a xylene mixture via conversion to and reconversion from naphthenes. The yield of xylenes in the product is enhanced by forming xylenes from ethylbenzene. The loss of $C_8$ aromatics through the reaction is low: typically less than about 4 wt-% per pass of $C_8$ aromatics in the feed to the reactor, preferably no more than about 3.5 wt-%, and most preferably less than 3 wt-%. In an aspect, the loss of $C_8$ aromatics may be referred to as ring loss.

Usually the isomerization conditions are sufficient that at least about 10%, preferably between about 20 and 50%, of the ethylbenzene in the feed stream is converted. In an aspect, the isomerization conditions may not result in a xylene equilibrium being reached. The mole ratio of xylenes in the product stream may be at least about 80%, say between about 85 and 95%, of equilibrium under the conditions of the isomerization. Where the isomerization process is to generate para-xylene, e.g., from meta-xylene, the feed stream may comprise less than 5 mass-% para-xylene and the isomerization product may comprise a para-xylene/xylenes mole ratio of between about 0.20:1 to 0.25:1. In an aspect, the UZM-55 catalyst of the present invention may isomerize ethylbenzene without performing much isomerization of xylenes. In such instance, the conversion of ethylbenzene may be between about 20 and about 50% of the ethylbenzene in the feedstream, but the ratio of p-xylene to total xylenes in the product stream (pX/X) may be less than 0.22 or less than 0.20.

The particular scheme employed to recover an isomerized product from the effluent of the reactors of the isomerization zone is not critical to the instant invention, and any effective recovery scheme known in the art may be used. Typically, the liquid product is fractionated to remove light and/or heavy byproducts to obtain the isomerized product. Heavy byproducts include $A_{10}$ compounds such as dimethylethylbenzene. In some instances, certain product species such as ortho-xylene or dimethylethylbenzene may be recovered from the isomerized product by selective fractionation. The product from isomerization of $C_8$ aromatics usually is processed to selectively recover the para-xylene isomer, optionally by crystallization or by selective adsorption using crystalline aluminosilicates according to U.S. Pat. No. 3,201,491, hereby incorporated herein by reference. Alternative adsorption recovery processes are described In U.S. Pat. Nos. 3,626,020; 3,696,107; 4,039,599; 4,184,943; 4,381,419 and 4,402,832, incorporated herein by reference.

In an aspect, a hydrocarbon stream may be contacted with a microporous crystalline zeolite having a channel system comprising ten-membered rings of tetrahedrally coordinated atoms and twelve-membered rings of tetrahedrally coordinated atoms in a single channel wherein said contact is at conversion conditions to provide a converted hydrocarbon product comprising a hydrocarbon compound not present in the hydrocarbon stream.

In order to more fully illustrate the invention, the following examples are set forth. It is to be understood that the examples are only by way of illustration and are not intended as an undue limitation on the broad scope of the invention as set forth in the appended claims.

Example 1

419.33 grams of 1,6-dibromohexane and 330.56 grams of N-methylpiperidine were combined in a 2-L Teflon bottle along with 749.90 grams of DI $H_2O$. The mixture was stirred with a Heidolph mixer at 1600 RPM and transitioned from a two-layer solution to homogeneous white opaque mixture overnight. Heat was slowly added until a temperature of around 50° C. to 70° C. was obtained. Within 72 hours, the solution had become yellow and clear, which indicated the reaction had gone to completion. Partway through, the solution is yellow on top with unreacted clear material on the bottom. In this synthesis, 14.9 g of clear, unreacted material was separated using a separatory funnel. $^{13}$C-NMR analysis determined that a solution comprising 1,6-bis(N-methylpiperidinium) hexane dibromide had been synthesized.

Example 2

1000 g of solution from Example 1 was poured into a round-bottom flask along with excess silver (I) oxide and the solution was allowed to stir for 24 hours at room temperature. After the reaction was complete (24 hours to 48 hours), the resulting material was filtered to remove the solid silver bromide and was allowed to sit in direct sunlight so that any remaining silver bromide would precipitate and fall out of solution. The filter/sun cycle was repeated four times before the solution remained clear and was deemed to be usable. It was then sent for water analysis and shown to comprise 67.4% water.

Example 3

Figure 4:
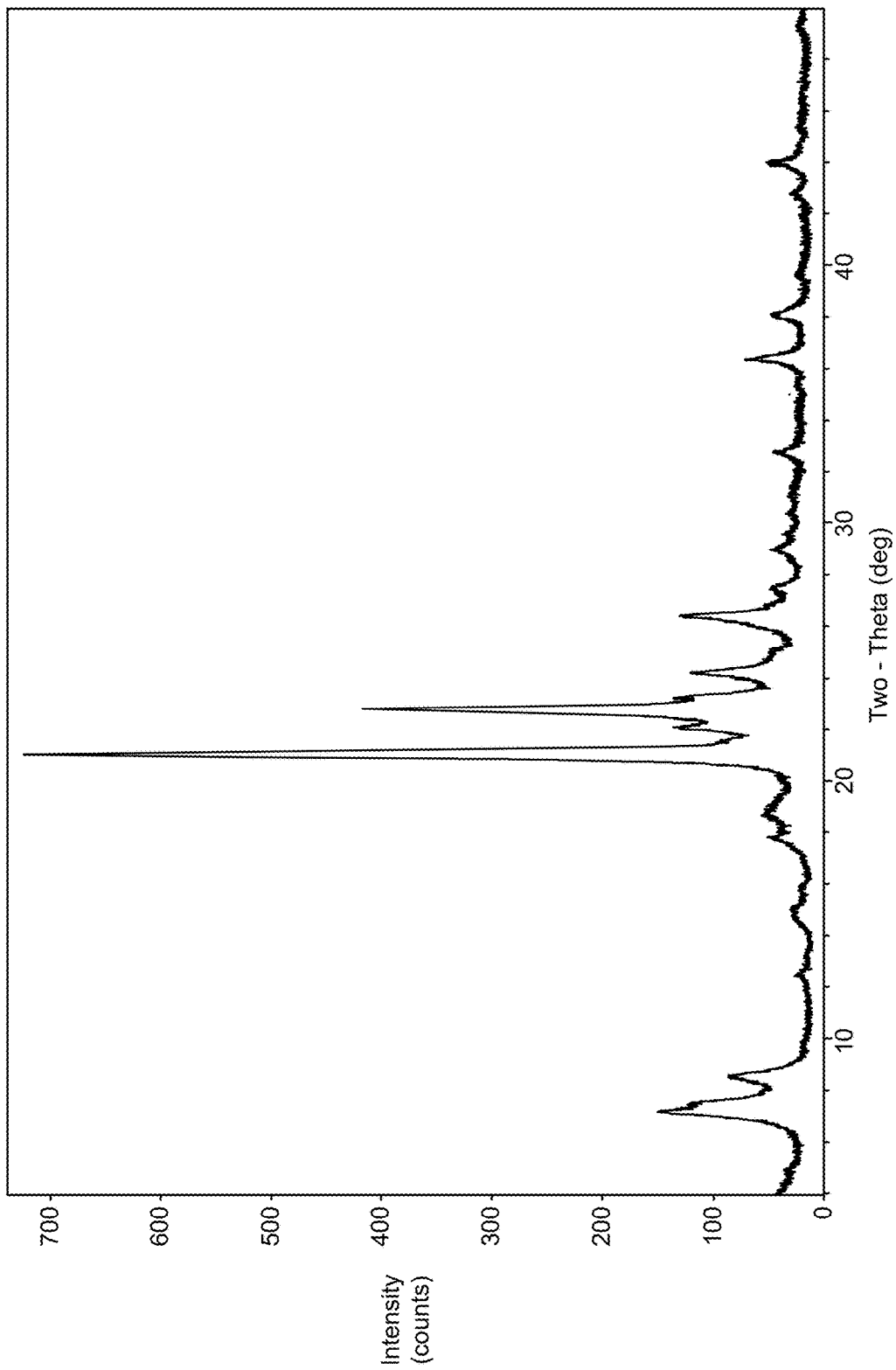
FIG. 4 is an XRD pattern of the UZM-55 zeolite formed in Example 3. This pattern shows the UZM-55 zeolite in the as-synthesized form.
Figure 5:
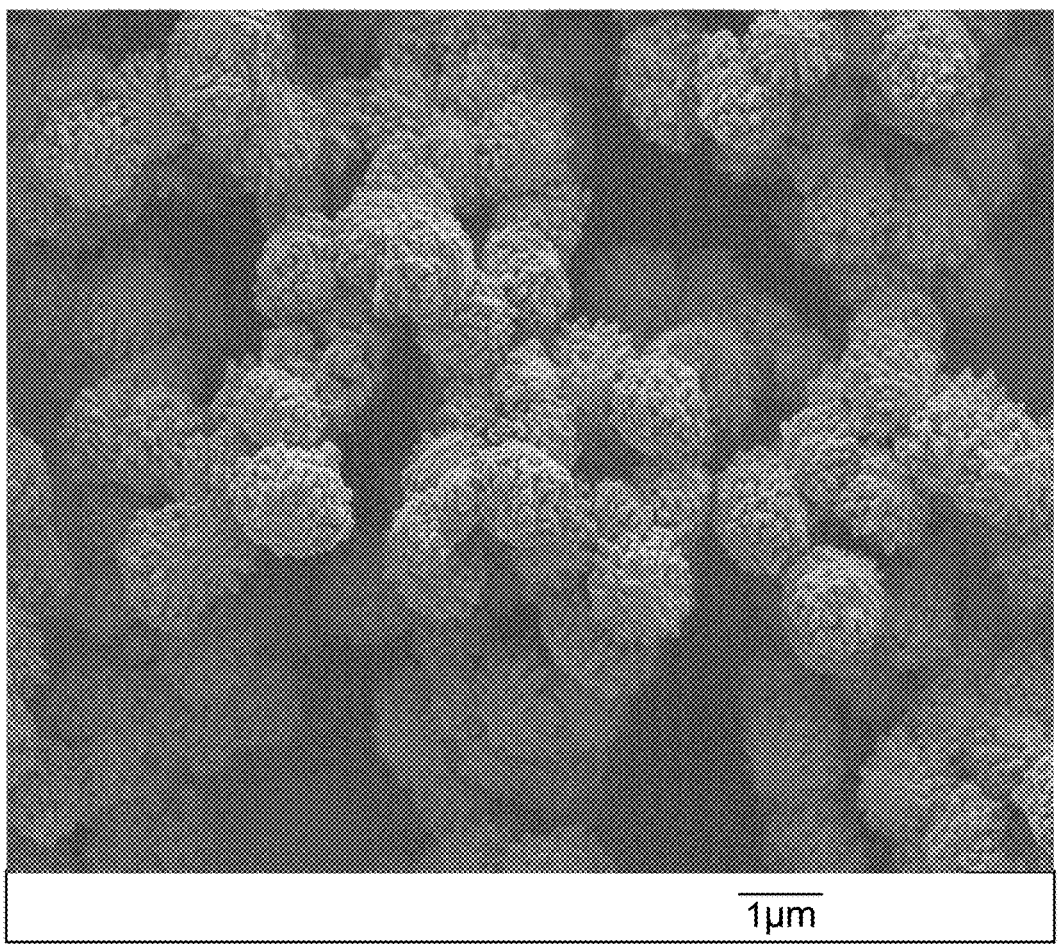
FIG. 5 is a high resolution SEM image of the UZM-55 zeolite formed in Example 3 at 1 μm resolution.
Figure 6:
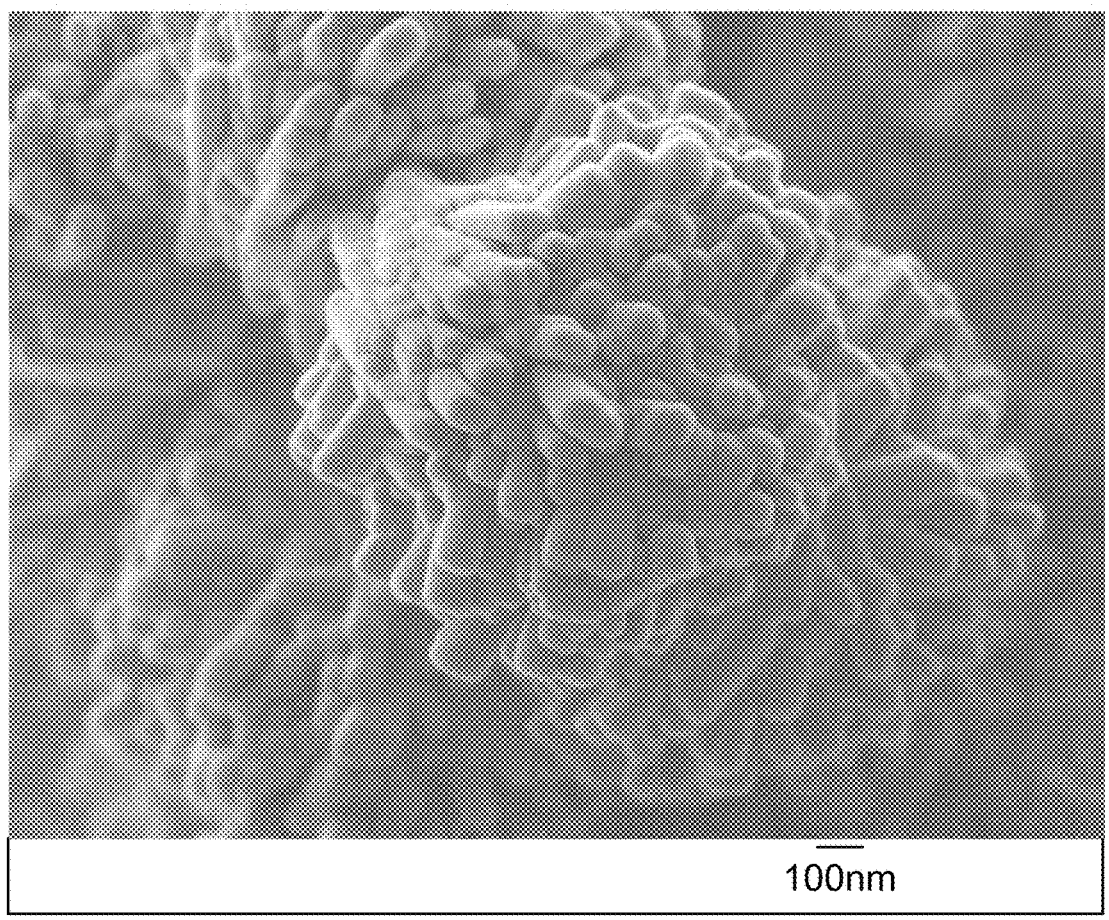
FIG. 6 is a high resolution SEM image of the UZM-55 zeolite formed in Example 3 at 100 nm resolution.
Figure 7:
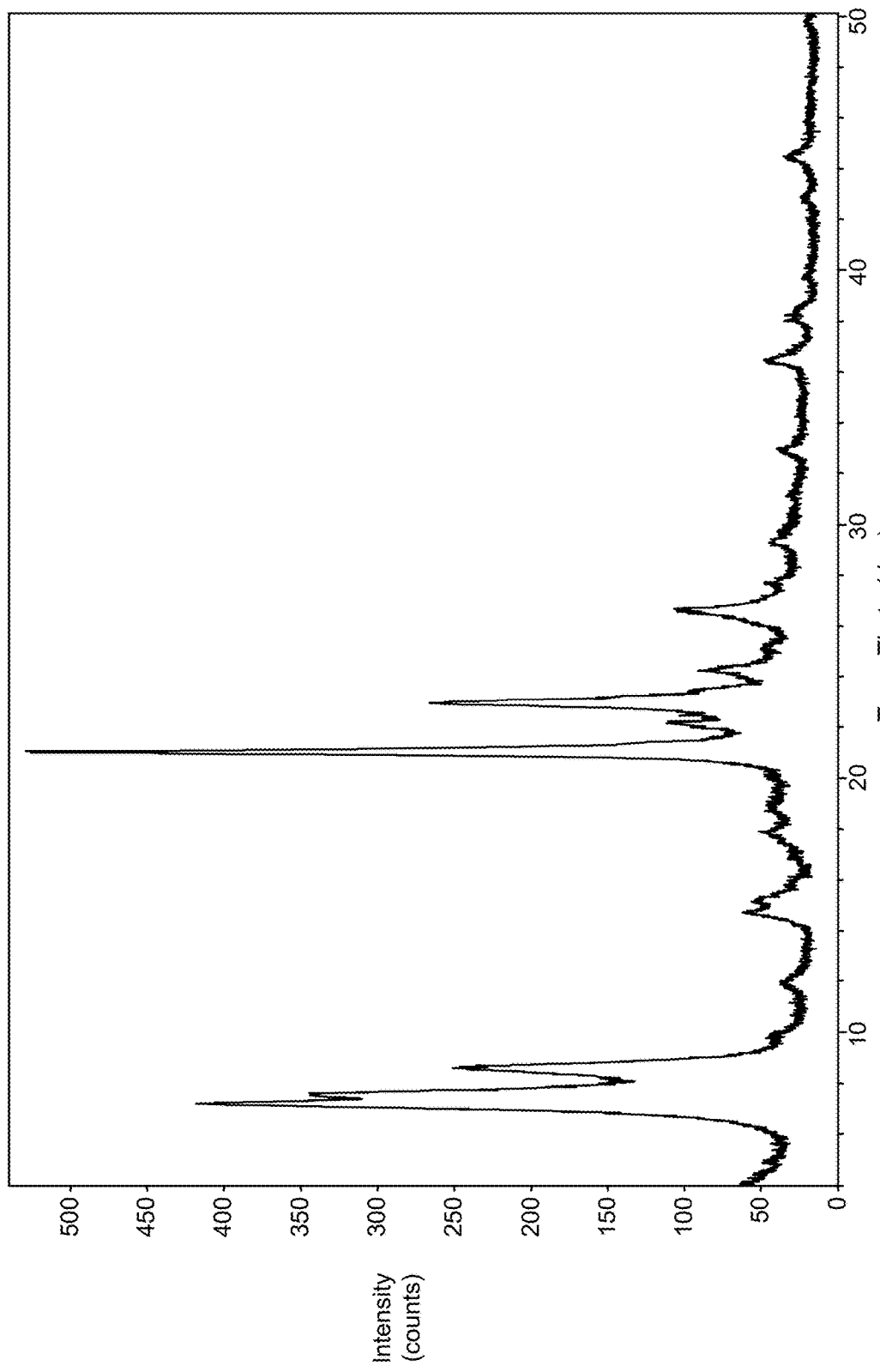
FIG. 7 is also an XRD pattern of the UZM-55 zeolite formed in Example 3. This pattern shows the UZM-55 zeolite after calcination.

50 g LudoxAS-40 was stirred into 48.74 g of the Example 2 solution, followed by the addition of 106.85 g water. After mixing thoroughly, this synthesis solution was transferred to a 300 cc stirred autoclave and digested for 6 days at 160° C. while stirring at 250 rpm. The product was dried. Analysis shows a LOI of 12.8 wt %, Si=47.2 wt %, Al=0.045 wt %, Na=0.04 wt % 7.47 wt % C, 0.976 wt % N for a carbon to nitrogen ratio of 9. The XRD pattern is shown in FIG. 4. High resolution SEM images are shown at two different length scales in FIGS. 5 and 6 respectively. The sample was then calcined under air for 4 hours at 600° C. Analysis shows a BET SA of 273 m$^2$/g, Langmuir SA of 400 m$^2$/g, total pore volume of 0.225 cc/g, and a micropore volume of 0.107 cc/g. The XRD pattern is shown in FIG. 7.

Example 4

43.33 grams LudoxAS-40 was stirred into a mixture of 1.63 grams of a 10 wt % KOH solution in water and 40.71 grams Example 2 product. 100.71 grams DI $H_2O$ was then stirred in. After mixing thoroughly 0.18 g. $H_3BO_3$ was added. The resulting synthesis mixture was loaded into a 300 cc stirred autoclave and digested for 6 days at 160° C. stirring at 250 rpm. The product was dried. Elemental analysis showed 47.1% Si (V.F.), 0.14% B with an LOI of 13.4%, C/N=9.53. XRD analysis identified the product as UZM-55.

Example 5

0.11 grams aluminum hydroxide (Pfaltz & Bauer) was combined with 41.12 grams of the Example 2 solution and stirred until all of the alumina had dissolved. 43.48 grams of Ludox AS-40 was then added along with 94.14 grams of DI $H_2O$. The resulting synthesis mixture was loaded into a 300 cc stirred autoclave and digested for 6 days at 160° C. stirring at 250 rpm. The product was dried. Elemental analysis shows 46.5% Si (V.F.), 0.31% Al with an LOI of 14.3%, C/N=9.55. XRD analysis identified the product as UZM-55. A portion of this product was calcined at 600° C. for 4 hours. Analysis shows a BET SA of 301 $m^2/g$, total pore volume of 0.235 cc/g, and a micropore volume of 0.120 cc/g.

Example 6

Figure 8:
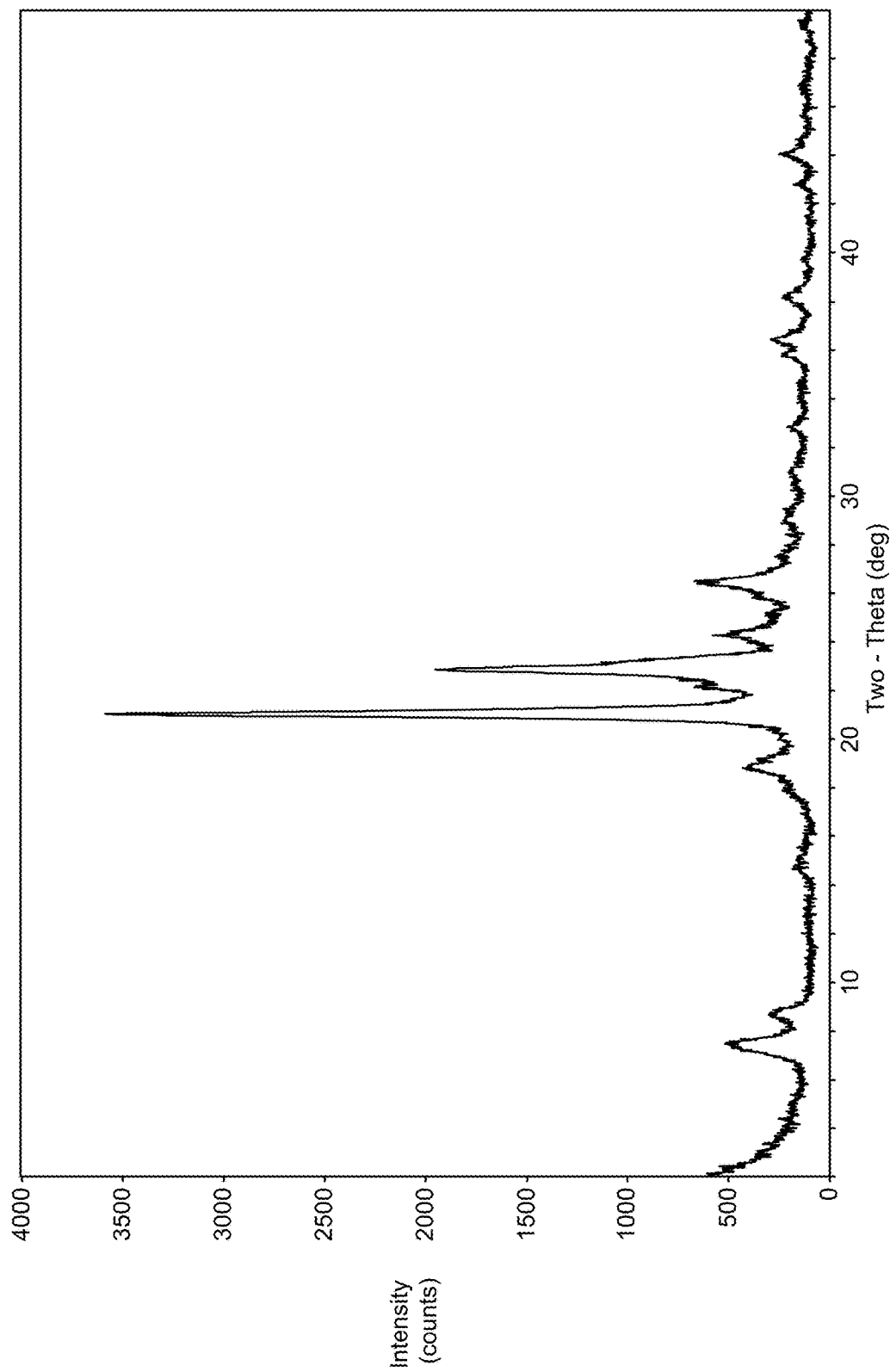
FIG. 8 is an XRD pattern of the UZM-55 zeolite formed in Example 6. This pattern shows the UZM-55 zeolite in the as-synthesized form.

1.25 grams of aluminum hydroxide (Pfaltz & Bauer) was combined with 274.29 grams of the Example 2 solution and stirred until all of the alumina had dissolved. 290.00 grams of Ludox AS-40 was then added along with 627.92 grams of DI $H_2O$. 0.79 g of the as-synthesized Example 3 product and 0.36 g of the calcined Example 3 product were then stirred in. The resulting synthesis mixture was loaded into a 2-L stirred autoclave and digested at 160° C. at 250 RPM for 210 hours. The resulting product was isolated via centrifugation and dried at 100° C. to remove any residual water. Analysis showed $SiO_2/Al_2O_3$=189, 40 ppm Na and LOI=13.0 wt %. The x-ray diffraction pattern is shown in FIG. 8. A portion of this product was calcined at 600° C. for 4 hours. Analysis shows a BET SA of 342 $m^2/g$, total pore volume of 0.339 cc/g, and a micropore volume of 0.112 cc/g.

Example 7

12.71 grams of 1,6-dibromohexane and 10.02 grams of N-Methylpiperidine were combined in a 125 cc Teflon bottle along with 22.72 grams of DI $H_2O$. The mixture was stirred with a Heidolph mixer at 1600 RPM over the weekend and transitioned from a two-layer solution to homogeneous white opaque mixture overnight to a clear yellow solution. This yellow solution was combined with 419.33 grams of 1,6-dibromohexane, 330.56 grams of N-Methylpiperidine and 749.90 grams of DI $H_2O$ in a 2 L Teflon bottle and stirred with the Heidolph stirrer. After 2 days, clear liquid still existed on the bottom, so small quantities of N-methylpiperidine were added over the next two days while stirring. After the weekend, the solution was completely yellow colored. $^{13}$C-NMR analysis determined that a solution comprising 1,6-bis(N-Methylpiperidinium)hexane dibromide had been synthesized.

Example 8

1000 grams of solution from Example 7 was poured into a round-bottom flask along with excess silver(I) oxide and the solution was allowed to stir for 24 hours at room temperature. After the reaction was complete (24-48 hours), the resulting material was filtered to remove the solid silver bromide and was allowed to sit in direct sunlight so that any remaining silver bromide would precipitate and fall out of solution. The filter/sun cycle was repeated four times before the solution remained clear and was deemed to be usable. It was then sent for water analysis and shown to comprise 67.4% water.

Example 9

16.66 grams of Ludox AS-40 was stirred into 16.25 g of the Example 8 solution, followed by the addition of 35.61 g water. After mixing thoroughly, this synthesis solution was transferred into 45 cc static autoclave and digested for 3 days at 175° C. The product was dried. XRD analysis identified the product as UZM-55.

Example 10

2 moles (508.29 grams) of 1,6-dibromohexane and 4 moles (400.69 grams) of N-methylpiperdine were combined in a 2-L Teflon bottle along with 908.98 grams of DI $H_2O$. The mixture was stirred with a Heidolph mixer at 1600 RPM and transitioned from a two-layer solution to a homogenous white opaque solution overnight. Heat was slowly added until a temperature of around 50° C. to 70° C. was obtained. Within 48 hours, the solution had become yellow and clear, which indicated the reaction had gone to completion.

Example 11

1221.4 grams of solution from Example 10 was poured into a round-bottom flask along with excess silver(I) oxide and the solution was allowed to stir for 24 hours at room temperature. After the reaction was complete (24 hours to 48 hours), the resulting material was filtered to remove the solid silver precipitate and was allowed to sit in direct sunlight so that any remaining silver bromide would fall out of solution. The filter/sun cycle was repeated four times before the solution remained clear and was deemed to be usable. It was then sent for water analysis and shown to comprise 67.6% water.

Example 12

0.63 grams aluminum isopropoxide (98%, Sigma Aldrich) was combined with 42.65 grams of the Example 11 solution and stirred until all of the alumina was dissolved. 43.48 grams of Ludox AS-40 was then added along with 92.62 grams of DI $H_2O$. 0.41 grams of pure $SiO_2$ UZM-55 was then stirred in. The resulting synthesis mixture was loaded into a 300 cc stirred autoclave and digested for 8 days at 160° C. stirring at 250 RPM. XRD analysis identified the product as UZM-55 with a MTW impurity.

Example 13

The UZM-55 catalyst of the invention (Catalyst A) was made by taking 20 g of the Example 6 product, extruding with gamma alumina (Versal-251 obtained from UOP) to obtain an extrudate comprising 12 wt % zeolite with the remainder alumina, drying and then calcining at 550° C. for 3 hours. Catalyst B (not of the invention) was made in the same way by using MTW zeolite synthesized by the methods of U.S. Pat. No. 8,247,630 to obtain an extrudate comprising 5 wt % zeolite. Catalysts A and B were then finished by impregnating a chloroplatinic acid solution to achieve 0.3 wt % Pt on the extrudates. Oxychlorination was then carried out a temperature of 565° C. for 3 hours using a 4.3M HCl solution flowing at 9 g/hr along with an air flow of 3 L/min. Reduction of the Pt in $H_2$ was carried out at 565° C. for 120 min. Finally, the extrudates were sulfided to 0.09 wt % S using 5 vol % $H_2S$ in $H_2$ overnight to yield the final catalysts C (UZM-55) and D (MTW).

Catalysts C and D were then tested at 380° C., 388° C., and 396° C. using a feed of 15% EB, 25 wt % oX, and 60 wt % mX to yield a product stream. Both catalyst were tested at 7 $h^{-1}$ WHSV while catalyst C was also tested at a WHSV of 5 $h^{-1}$. Table 5 shows data resulting from the test.

|  | Catalyst C | | | | | | Catalyst D | | |
| --- | --- | --- | --- | --- | --- | --- | --- | --- | --- |
|  | WHSV | | | | | | | | |
|  | 7 | | | 5 | | | 7 | | |
| Temperature | 380 | 388 | 396 | 380 | 388 | 396 | 380 | 388 | 396 |
| pressure | 81 | 96 | 111 | 80 | 95 | 110 | 81 | 96 | 111 |
| EB Conversion | 29.8 | 33.3 | 35.8 | 33.7 | 37.6 | 40.5 | 34.3 | 38.4 | 41.4 |
| pX/X | 0.173 | 0.191 | 0.205 | 0.195 | 0.210 | 0.221 | 0.215 | 0.226 | 0.232 |
| C8 Ring loss | 1.02 | 1.39 | 1.88 | 1.42 | 1.90 | 2.50 | 1.78 | 2.39 | 3.10 |

Figure 9:
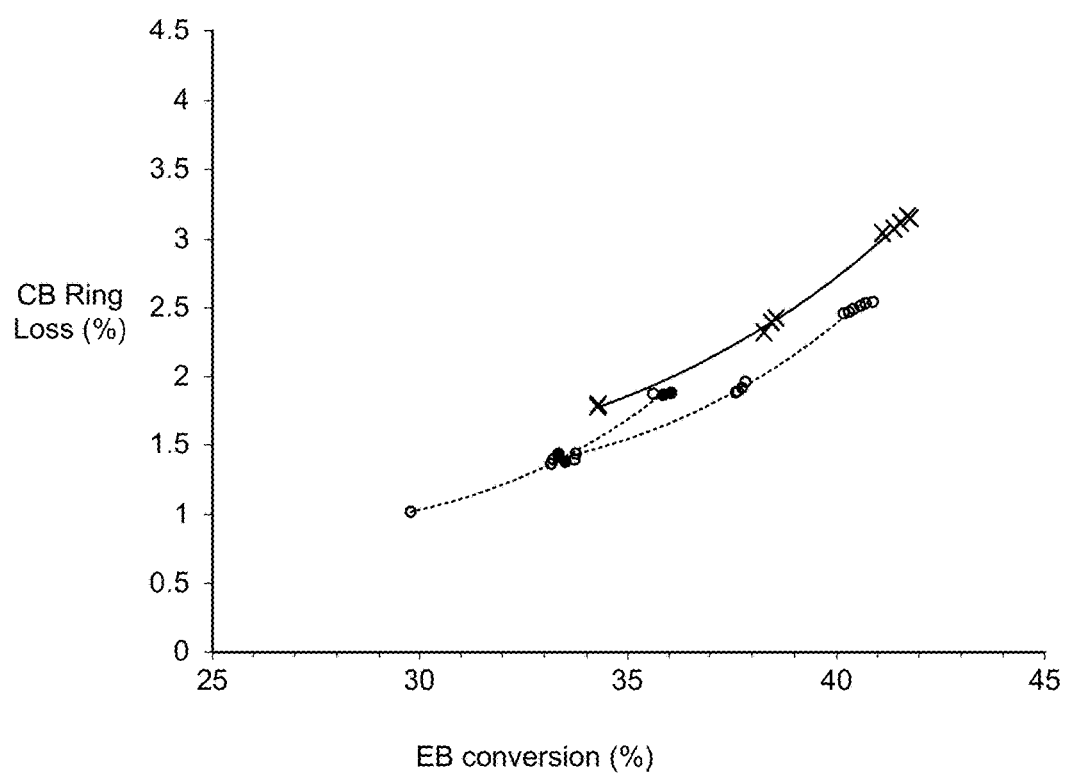
FIG. 9 is a graph of the ring loss in molecules containing 8 carbon atoms and a ring as a function of the ethylbenzene conversion as described in Example 13.
Figure 10:
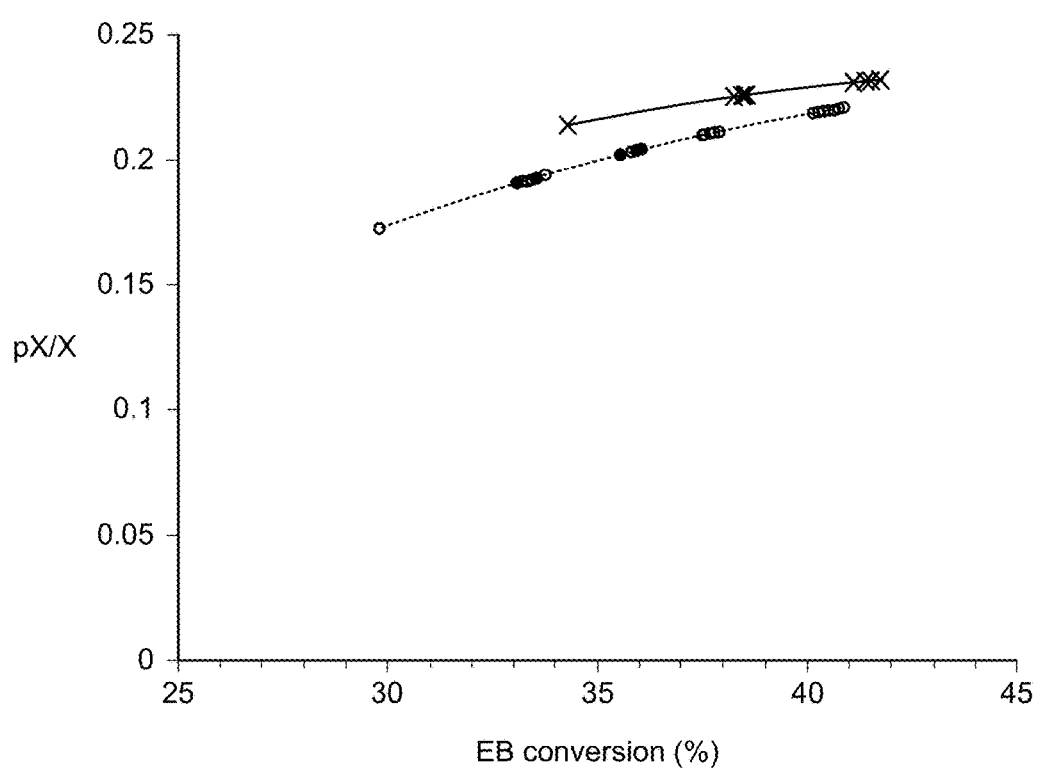
FIG. 10 is a graph of the ratio of para-xylene to the total xylenes in the product effluent as a function of the ethylbenzene conversion as described in Example 13.

The data is then plotted graphically in FIGS. 9 and 10. FIG. 9 shows a graph of the ring loss in molecules containing 8 carbon atoms and a ring as a function of the ethylbenzene conversion. The ring loss is calculated as a percentage yield loss of C8 Rings from the inlet to the outlet of the reactor. The C8 rings include Xylenes, EB, and C8 naphthenes (ethylcyclohexane, trimethylcyclopentanes, methylethylcyclopentanes and dimethylcyclohexanes). FIG. 10 shows a graph of the ratio of para-xylene to the total xylenes in the product effluent as a function of the ethylbenzene conversion. For both FIGS. 9 and 10, the data from Catalyst D (not of the invention) is represented as X on the plots. The data from Catalyst C at 7 WHSV is represented in closed circles and the data from Catalyst C at 5 WHSV is represented in open circles. The catalyst comprising UZM-55 has significantly lower ring loss at equivalent ethylbenzene conversion as the catalyst comprising MTW. UZM-55 is also active for the isomerization of ethylbenzene to one or more xylenes selected from the group consisting of p-xylene, m-xylene, o-xylene, and combinations thereof and for the isomerization of ortho- and/or meta-xylene to mixed xylenes comprising para-xylene.

Specific Embodiments

While the following is described in conjunction with specific embodiments, it will be understood that this description is intended to illustrate and not limit the scope of the preceding description and the appended claims.

A first embodiment of the invention is a process for the isomerization of ethylbenzene comprising contacting a feed stream comprising ethylbenzene with a catalyst comprising a microporous crystalline zeolite to yield a product stream higher in xylene content than the feed stream where the microporous crystalline zeolite is represented by an empirical formula $M_m^{n+}R_rAl_xE_ySiO_z$ where M represents hydrogen or a metal or metals selected from the group consisting of zinc, Group 1 (IUPAC 1) metals, Group 2 (IUPAC 2) metals, Group 3 (IUPAC 3) metals or lanthanide series metals of the periodic table, "m" is the mole ratio of M to Si and varies from 0 to about 1.0, "n" is the weighted average valence of M and has a value of about 1 to about 3, R is a structure directing agent or agents, "r" is the mole ratio of N from the organic structure directing agent or agents to Si and has a value of about 0 to about 1.0, "x" is the mole ratio of Al to Si and has a value of from 0 to about 0.026, E is an element selected from the group consisting of gallium, iron, boron and mixtures thereof, "y" is the mole ratio of E to Si and has a value from 0 to about 0.026, and "z" is the mole ratio of O to (Al+E) and has a value determined by the equation z=(4+m+3♦x+3♦y)/2. An embodiment of the invention is one, any or all of prior embodiments in this paragraph up through the first embodiment in this paragraph wherein the microporous crystalline zeolite is characterized in that it has the x-ray diffraction pattern having at least the d-spacings and intensities set forth in Table 1:

TABLE 1

| 2θ | d(Å) | I/I₀ % |
| --- | --- | --- |
| 7.16 | 12.34 | VW-W |
| 7.44 | 11.87 | VW-W |
| 8.58 | 10.30 | VW |
| 21.01* | 4.225 | VS |
| 22.07 | 4.024 | VW |
| 22.75 | 3.906 | MW-M |
| 24.19 | 3.676 | VW |
| 26.41 | 3.372 | VW-W |
| 32.73 | 2.734 | VW |
| 36.37 | 2.468 | VW |
| 44.01 | 2.056 | VW |

An embodiment of the invention is one, any or all of prior embodiments in this paragraph up through the first embodiment in this paragraph wherein the microporous crystalline zeolite in a calcined form exhibits an XRD pattern as shown in Table 2:

TABLE 2

| 2θ | d(Å) | I/I₀ % |
| --- | --- | --- |
| 7.19 | 12.28 | MW-S |
| 7.57 | 11.67 | W-M |
| 8.59 | 10.29 | W-MW |
| 14.72 | 6.013 | VW |
| 21.04* | 4.219 | VS |
| 22.15 | 4.010 | VW |
| 23.03 | 3.859 | MW-M |
| 24.34 | 3.654 | VW |
| 26.63 | 3.345 | VW-W |
| 36.47 | 2.462 | VW |
| 44.49 | 2.035 | VW |

An embodiment of the invention is one, any or all of prior embodiments in this paragraph up through the first embodiment in this paragraph wherein x is less than 0.02. An embodiment of the invention is one, any or all of prior embodiments in this paragraph up through the first embodiment in this paragraph wherein y is less than 0.02. An embodiment of the invention is one, any or all of prior embodiments in this paragraph up through the first embodiment in this paragraph wherein r is from about 0.0005 to about 0.08. An embodiment of the invention is one, any or all of prior embodiments in this paragraph up through the first embodiment in this paragraph wherein the microporous crystalline zeolite is thermally stable up to a temperature of at least 600° C. An embodiment of the invention is one, any or all of prior embodiments in this paragraph up through the first embodiment in this paragraph wherein the microporous crystalline zeolite has an $SiO_2/Al_2O_3$ ratio greater than 75. An embodiment of the invention is one, any or all of prior embodiments in this paragraph up through the first embodiment in this paragraph wherein the microporous crystalline zeolite has an $SiO_2/Al_2O_3$ ratio greater than 150. An embodiment of the invention is one, any or all of prior embodiments in this paragraph up through the first embodiment in this paragraph wherein the microporous crystalline zeolite M is selected from the group consisting of lithium, potassium, rubidium, cesium, magnesium, calcium, strontium, barium, zinc, yttrium, lanthanum and gadolinium. An embodiment of the invention is one, any or all of prior embodiments in this paragraph up through the first embodiment in this paragraph wherein the microporous crystalline zeolite R is 1,6-bis(N-methylpiperidinium)hexane. An embodiment of the invention is one, any or all of prior embodiments in this paragraph up through the first embodiment in this paragraph wherein the microporous crystalline zeolite has a micropore volume of greater than 0.08 mL/g and less than 0.15 mL/g. An embodiment of the invention is one, any or all of prior embodiments in this paragraph up through the first embodiment in this paragraph wherein the isomerization conditions include a temperature of about 300° C. to about 450° C. An embodiment of the invention is one, any or all of prior embodiments in this paragraph up through the first embodiment in this paragraph wherein the isomerization conditions include a pressure of about 70 psig to about 130 psig. An embodiment of the invention is one, any or all of prior embodiments in this paragraph up through the first embodiment in this paragraph wherein the isomerization conditions include a weight hourly space velocity of about 5 h$^{-1}$ to about 7 h$^{-1}$. An embodiment of the invention is one, any or all of prior embodiments in this paragraph up through the first embodiment in this paragraph wherein the feed stream also comprises hydrogen and one or more xylenes selected from the group consisting of p-xylene, m-xylene, o-xylene and combinations thereof. An embodiment of the invention is one, any or all of prior embodiments in this paragraph up through the first embodiment in this paragraph wherein the catalyst also comprises a hydrogenation function selected from a noble metal and a base metal, and a binder. An embodiment of the invention is one, any or all of prior embodiments in this paragraph up through the first embodiment in this paragraph wherein the product stream has a higher para-xylene content than the feed stream.

A second embodiment of the invention is a process for the isomerization of ethylbenzene and xylenes comprising contacting a feed stream comprising ethylbenzene and xylenes with a catalyst comprising a microporous crystalline zeolite to yield a product stream higher in xylene content than the feed stream where the microporous crystalline zeolite is represented by an empirical formula $M_m^{n+}R_rAl_xE_ySiO_z$ where M represents hydrogen or a metal or metals selected from the group consisting of zinc, Group 1 (IUPAC 1) metals, Group 2 (IUPAC 2) metals, Group 3 (IUPAC 3) metals or lanthanide series metals of the periodic table, "m" is the mole ratio of M to Si and varies from 0 to about 1.0, "n" is the weighted average valence of M and has a value of about 1 to about 3, R is a structure directing agent or agents, "r" is the mole ratio of N from the organic structure directing agent or agents to Si and has a value of about 0 to about 1.0, "x" is the mole ratio of Al to Si and has a value of from 0 to about 0.026, E is an element selected from the group consisting of gallium, iron, boron and mixtures thereof, "y" is the mole ratio of E to Si and has a value from 0 to about 0.026, and "z" is the mole ratio of O to (Al+E) and has a value determined by the equation z=(4+m+3♦x+3♦y)/2.

A third embodiment of the invention is a process for the isomerization of ethylbenzene and xylenes comprising contacting a feed stream comprising ethylbenzene and xylenes with a catalyst comprising a microporous crystalline zeolite to yield a product stream higher in para-xylene content than the feed stream where the microporous crystalline zeolite is represented by an empirical formula $M_m^{n+}R_rAl_xE_ySiO_z$ where M represents hydrogen or a metal or metals selected from the group consisting of zinc, Group 1 (IUPAC 1) metals, Group 2 (IUPAC 2) metals, Group 3 (IUPAC 3) metals or lanthanide series metals of the periodic table, "m" is the mole ratio of M to Si and varies from 0 to about 1.0, "n" is the weighted average valence of M and has a value of about 1 to about 3, R is a structure directing agent or agents, "r" is the mole ratio of N from the organic structure directing agent or agents to Si and has a value of about 0 to about 1.0, "x" is the mole ratio of Al to Si and has a value of from 0 to about 0.026, E is an element selected from the group consisting of gallium, iron, boron and mixtures thereof, "y" is the mole ratio of E to Si and has a value from 0 to about 0.026, and "z" is the mole ratio of O to (Al+E) and has a value determined by the equation z=(4+m+3♦x+3♦y)/2, wherein ethylbenzene in the feed stream is greater than equilibrium, xylenes in the feed stream are lower than equilibrium, and para-xylene in the product is at or below equilibrium, but higher than content in feed stream.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for the isomerization of ethylbenzene comprising:
    contacting a feed stream comprising ethylbenzene with a catalyst comprising a microporous crystalline zeolite under isomerization conditions to yield a product stream having a higher xylene content than the feed stream where the microporous crystalline zeolite, after calcination and on an anhydrous basis, is represented by an empirical formula:

$$M_m^{n+}Al_xE_ySiO_z$$

where M represents hydrogen or a metal or metals selected from the group consisting of zinc, Group 1 (IUPAC 1)

metals, Group 2 (IUPAC 2) metals, Group 3 (IUPAC 3) metals or lanthanide series metals of the periodic table, "m" is the mole ratio of M to Si and varies from 0 to about 1.0, "n" is the weighted average valence of M and has a value of about 1 to about 3, "x" is the mole ratio of Al to Si and has a value of from 0 to about 0.026, E is an element selected from the group consisting of gallium, iron, boron and mixtures thereof, "y" is the mole ratio of E to Si and has a value from 0 to about 0.026, and "z" is the mole ratio of O to (Al+E) and has a value determined by the equation: $z=(4+m+3\bullet x+3\bullet y)/2$;

wherein the microporous crystalline zeolite in a calcined form exhibits an XRD pattern as shown in the table below

| 2θ | d(Å) | I/I₀ % |
|---|---|---|
| 7.19 | 12.28 | MW-S |
| 7.57 | 11.67 | W-M |
| 8.59 | 10.29 | W-MW |
| 14.72 | 6.013 | VW |
| 21.04* | 4.219 | VS |
| 22.15 | 4.010 | VW |
| 23.03 | 3.859 | MW-M |
| 24.34 | 3.654 | VW |
| 26.63 | 3.345 | VW-W |
| 36.47 | 2.462 | VW |
| 44.49 | 2.035 | VW. |

2. The process of claim 1 wherein x is less than 0.02.

3. The process of claim 1 wherein y is less than 0.02.

4. The process of claim 1 wherein the microporous crystalline zeolite is thermally stable up to a temperature of at least 600° C.

5. The process of claim 1 wherein the microporous crystalline zeolite has an $SiO_2/Al_2O_3$ ratio greater than 75.

6. The process of claim 1 wherein the microporous crystalline zeolite has an $SiO_2/Al_2O_3$ ratio greater than 150.

7. The process of claim 1 wherein M is selected from the group consisting of lithium, potassium, rubidium, cesium, magnesium, calcium, strontium, barium, zinc, yttrium, lanthanum and gadolinium.

8. The process of claim 1 wherein the microporous crystalline zeolite has a micropore volume of greater than 0.08 mL/g and less than 0.15 mL/g.

9. The process of claim 1 wherein the isomerization conditions include a temperature of about 300° C. to about 450° C.

10. The process of claim 1 wherein the isomerization conditions include a pressure of about 70 psig to about 130 psig.

11. The process of claim 1 wherein the isomerization conditions include a weight hourly space velocity of about 5 h$^{-1}$ to about 7 h$^{-1}$.

12. The process of claim 1 wherein the feed stream also comprises hydrogen and one or more xylenes selected from the group consisting of p-xylene, m-xylene, o-xylene and combinations thereof.

13. The process of claim 1 wherein the catalyst also comprises a hydrogenation function selected from a noble metal and a base metal, and a binder.

14. The process of claim 1 wherein the product stream has a higher para-xylene content than the feed stream.

15. A process for the isomerization of ethylbenzene and xylenes comprising:

contacting a feed stream comprising ethylbenzene and xylenes with a catalyst comprising a microporous crystalline zeolite under isomerization conditions to yield a product stream having a higher xylene content than the feed stream where the microporous crystalline zeolite, after calcination and on an anhydrous basis, is represented by an empirical formula:

$M_m^{n+}Al_xE_ySiO_z$ where M represents hydrogen or a metal or metals selected from the group consisting of zinc, Group 1 (IUPAC 1) metals, Group 2 (IUPAC 2) metals, Group 3 (IUPAC 3) metals or lanthanide series metals of the periodic table, "m" is the mole ratio of M to Si and varies from 0 to about 1.0, "n" is the weighted average valence of M and has a value of about 1 to about 3, "x" is the mole ratio of Al to Si and has a value of from 0 to about 0.026, E is an element selected from the group consisting of gallium, iron, boron and mixtures thereof, "y" is the mole ratio of E to Si and has a value from 0 to about 0.026, and "z" is the mole ratio of O to (Al+E) and has a value determined by the equation: $z=(4+m+3\blacklozenge x+3\blacklozenge y)/2$;

wherein the microporous crystalline zeolite in a calcined form exhibits an XRD pattern as shown in the table below

| 2θ | d(Å) | I/I₀ % |
|---|---|---|
| 7.19 | 12.28 | MW-S |
| 7.57 | 11.67 | W-M |
| 8.59 | 10.29 | W-MW |
| 14.72 | 6.013 | VW |
| 21.04* | 4.219 | VS |
| 22.15 | 4.010 | VW |
| 23.03 | 3.859 | MW-M |
| 24.34 | 3.654 | VW |
| 26.63 | 3.345 | VW-W |
| 36.47 | 2.462 | VW |
| 44.49 | 2.035 | VW. |

16. A process for the isomerization of ethylbenzene and xylenes comprising:

contacting a feed stream comprising ethylbenzene and xylenes with a catalyst comprising a microporous crystalline zeolite under isomerization conditions to yield a product stream having a higher xylene content than the feed stream where the microporous crystalline zeolite, after calcination and on an anhydrous basis, is represented by an empirical formula:

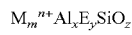
$M_m^{n+}Al_xE_ySiO_z$ where M represents hydrogen or a metal or metals selected from the group consisting of zinc, Group 1 (IUPAC 1) metals, Group 2 (IUPAC 2) metals, Group 3 (IUPAC 3) metals or lanthanide series metals of the periodic table, "m" is the mole ratio of M to Si and varies from 0 to about 1.0, "n" is the weighted average valence of M and has a value of about 1 to about 3, "x" is the mole ratio of Al to Si and has a value of from 0 to about 0.026, E is an element selected from the group consisting of gallium, iron, boron and mixtures thereof, "y" is the mole ratio of E to Si and has a value from 0 to about 0.026, and "z" is the mole ratio of O to (Al+E) and has a value determined by the equation: $z=(4+m+3\blacklozenge x+3\blacklozenge y)/2$;

wherein ethyl benzene in the feed stream is greater than equilibrium, xylenes in the feed stream are lower than equilibrium, and para-xylene in the product is at or below equilibrium, but higher than content in feed stream wherein the microporous crystalline zeolite in a calcined form exhibits an XRD pattern as shown in the table below

| 2θ | d(Å) | I/I₀ % |
|---|---|---|
| 7.19 | 12.28 | MW-S |
| 7.57 | 11.67 | W-M |
| 8.59 | 10.29 | W-MW |
| 14.72 | 6.013 | VW |
| 21.04* | 4.219 | VS |
| 22.15 | 4.010 | VW |
| 23.03 | 3.859 | MW-M |
| 24.34 | 3.654 | VW |
| 26.63 | 3.345 | VW-W |
| 36.47 | 2.462 | VW |
| 44.49 | 2.035 | VW. |

\* \* \* \* \*